United States Patent
Rondoni et al.

(10) Patent No.: US 11,229,394 B2
(45) Date of Patent: Jan. 25, 2022

(54) PLATFORM FOR SECURE COMMUNICATIONS WITH MEDICAL DEVICE

(71) Applicant: INSPIRE MEDICAL SYSTEMS, INC., Golden Valley, MN (US)

(72) Inventors: John Rondoni, Maple Grove, MN (US); Dave Dieken, Maple Grove, MN (US)

(73) Assignee: INSPIRE MEDICAL SYSTEMS, INC., Golden Valley, MN (US)

( * ) Notice: Subject to any disclaimer, the term of this patent is extended or adjusted under 35 U.S.C. 154(b) by 449 days.

(21) Appl. No.: 15/751,056

(22) PCT Filed: Aug. 11, 2016

(86) PCT No.: PCT/US2016/046600
§ 371 (c)(1),
(2) Date: Feb. 7, 2018

(87) PCT Pub. No.: WO2017/027729
PCT Pub. Date: Feb. 16, 2017

(65) Prior Publication Data
US 2020/0086128 A1  Mar. 19, 2020

Related U.S. Application Data

(60) Provisional application No. 62/203,435, filed on Aug. 11, 2015.

(51) Int. Cl.
*A61N 1/372* (2006.01)
*G06F 21/60* (2013.01)
(Continued)

(52) U.S. Cl.
CPC ............ *A61B 5/361* (2021.01); *A61B 5/4836* (2013.01); *A61N 1/37254* (2017.08);
(Continued)

(58) Field of Classification Search
CPC .................................................. A61N 1/37254
See application file for complete search history.

(56) References Cited

U.S. PATENT DOCUMENTS 6,804,558 B2   10/2004   Haller et al.
7,060,031 B2   6/2006    Webb et al.
(Continued)

FOREIGN PATENT DOCUMENTS

GN   101682628 A   3/2010
JP   2007524456 A  8/2007
(Continued)

OTHER PUBLICATIONS

Dwoskin, Securing the use of sensitive data on remote devices using a hardware-software architecture, Jun. 2010, 6 pages.
(Continued)

*Primary Examiner* — Michael W Kahelin
(74) *Attorney, Agent, or Firm* — Dicke, Billig & Czaja, PLLC

(57) ABSTRACT

A communication platform at least partially implements secure communications between a medical device and a trusted authority (TA) service provider. The secure communications prevent access to the secure communications by the communication platform while permitting access to the secure communications at the medical device and/or at the trusted authority service provider.

19 Claims, 15 Drawing Sheets

(51) Int. Cl.
*G06F 21/62* (2013.01)
*A61B 5/361* (2021.01)
*A61B 5/00* (2006.01)
*H04W 12/084* (2021.01)

(52) U.S. Cl.
CPC ....... *A61N 1/37282* (2013.01); *G06F 21/606* (2013.01); *G06F 21/6245* (2013.01); *H04W 12/084* (2021.01)

(56) References Cited

U.S. PATENT DOCUMENTS

| | | |
|---|---|---|
| 7,460,910 B2 | 12/2008 | Webb |
| 8,239,025 B2 | 8/2012 | Reinke |
| 8,295,938 B2 | 10/2012 | Goetz et al. |
| 8,347,365 B2 | 1/2013 | Jelatis et al. |
| 8,417,339 B2 | 4/2013 | Doerr et al. |
| 8,868,794 B2 | 10/2014 | Masoud et al. |
| 9,723,433 B2 | 8/2017 | Masoud et al. |
| 2002/0123673 A1 | 9/2002 | Webb et al. |
| 2006/0156416 A1 | 7/2006 | Huotar et al. |
| 2008/0058773 A1* | 3/2008 | John ............... A61M 5/1723 604/891.1 |
| 2008/0082830 A1 | 4/2008 | Goulet |
| 2008/0244717 A1* | 10/2008 | Jelatis ............... H04L 63/08 726/5 |
| 2010/0292556 A1 | 11/2010 | Golden |
| 2011/0015693 A1 | 1/2011 | Williamson |
| 2011/0161111 A1* | 6/2011 | Dicks ............... G06Q 50/24 705/3 |
| 2012/0215285 A1 | 8/2012 | Tahmasian et al. |
| 2013/0210365 A1 | 8/2013 | Karuppiah et al. |
| 2013/0290735 A1 | 10/2013 | Rombouts |
| 2015/0065047 A1 | 3/2015 | Wu et al. |
| 2015/0073498 A1 | 3/2015 | Kothandaraman |
| 2020/0178802 A1 | 6/2020 | Legay et al. |

FOREIGN PATENT DOCUMENTS

| | | |
|---|---|---|
| JP | 2007529274 A | 10/2007 |
| WO | 2005000397 A1 | 1/2005 |
| WO | 2005091205 A2 | 9/2005 |
| WO | 2008021920 | 2/2008 |
| WO | 2017027729 | 2/2017 |

OTHER PUBLICATIONS

Hirsch et al., FDA taking on cybersecurity risks for medical devices, Lawflash, Jun. 17, 2013, 3 pages.
Horowitz, iPad app remotely monitors pacemakers, defibrillators, eWEEK, Dec. 20, 2011, 2 pages.
Agrawal, Protection for Mobile Apps—There's a Patent App for That, Bookoff McAndrews, Apr. 18, 2013.
Sametinger et al., Security Challenges for Medical Devices, Communications of the ACM, vol. 58, No. 4, pp. 74-82.
Xu et al., IMDGuard: Securing Implantable Medical Devices with the External Wearable Guardian, IEEE Infocom, 2011, 9 pages.
Van Oorschot et al., Hardware-assisted circumvention of self-hashing software tamper resistance, IEE Trans. on Dependable and Secure Computing, Issue No. 02, Apr.-Jun. 2005, 13 pages.
Versel, Smartphone platform shows promise as 'artificial pancreas' to control diabetes, Chester Street Publishing, Inc., 2015,9 pages.
Finetech Medical, What is an Active Implantable Medical Device?, Finetech Medical, 2008, 2 pages.
PCT, International Preliminary Report on Patentability, PCT/US2016/046600, dated Feb. 22, 2018, 13 pages.

* cited by examiner

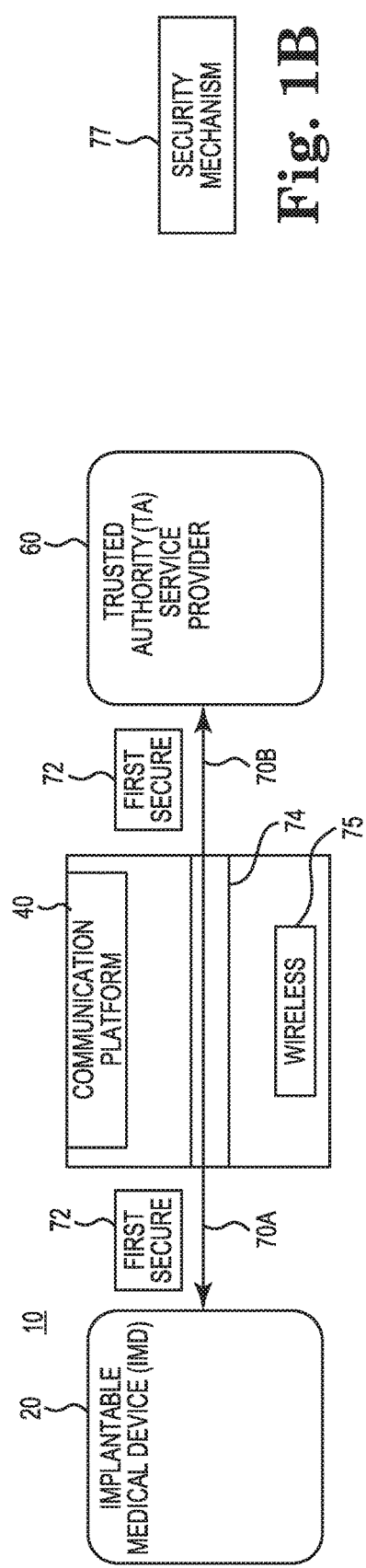
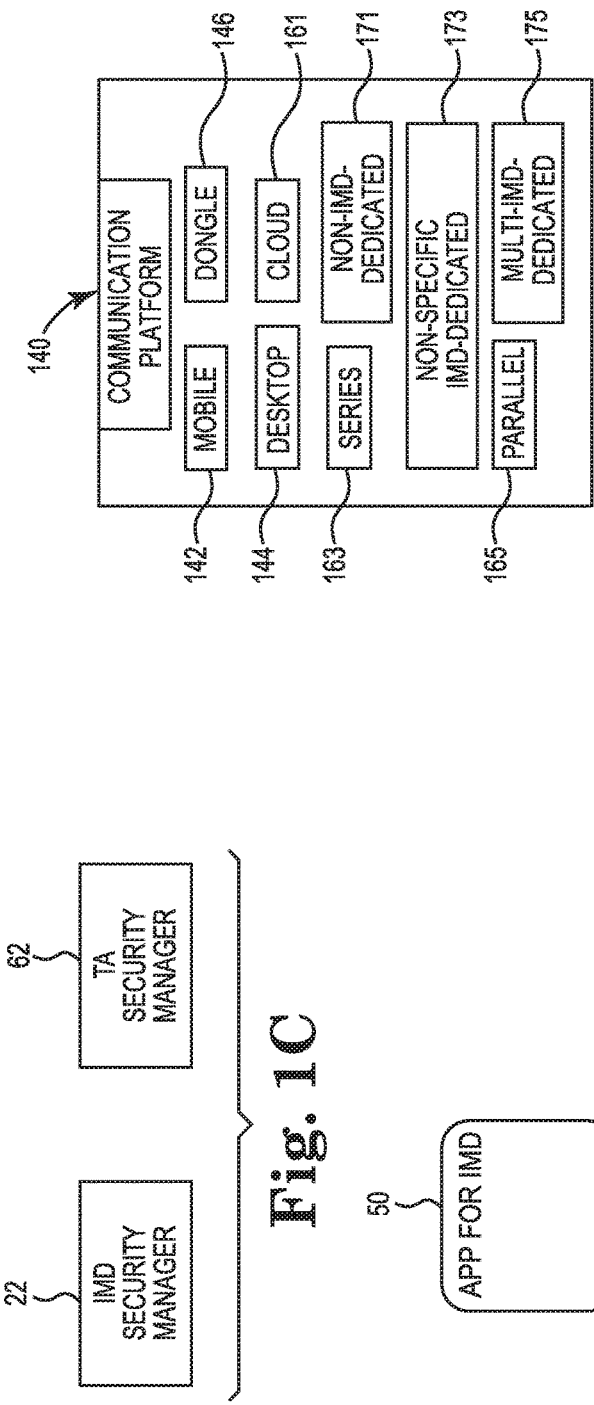

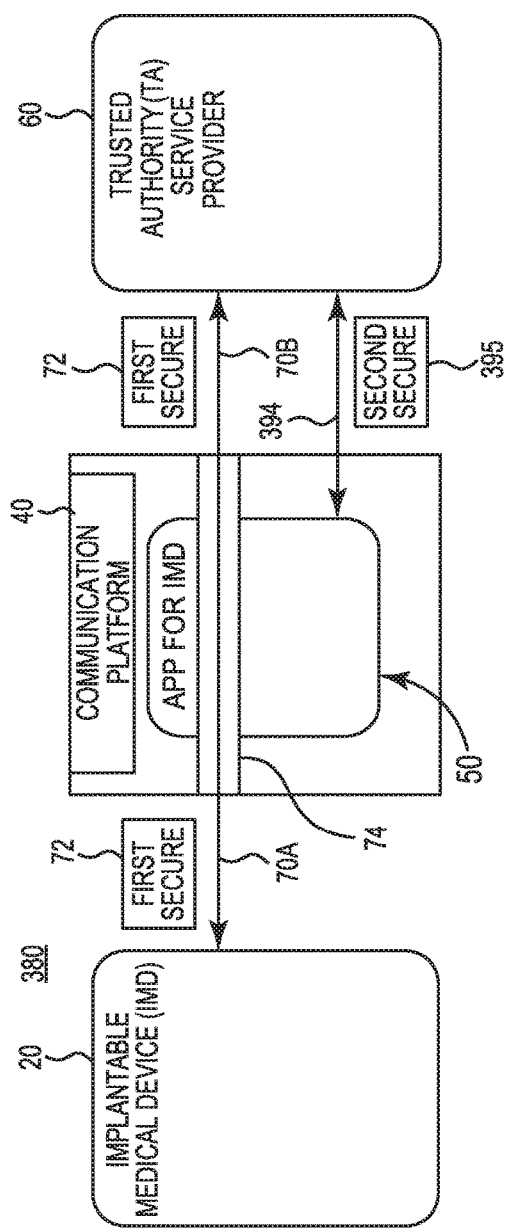
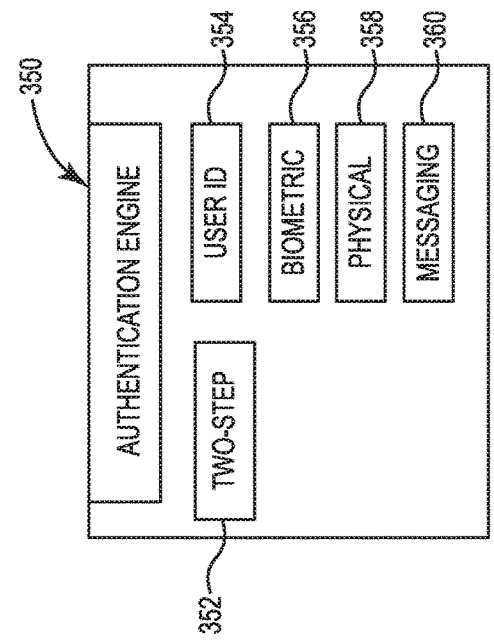
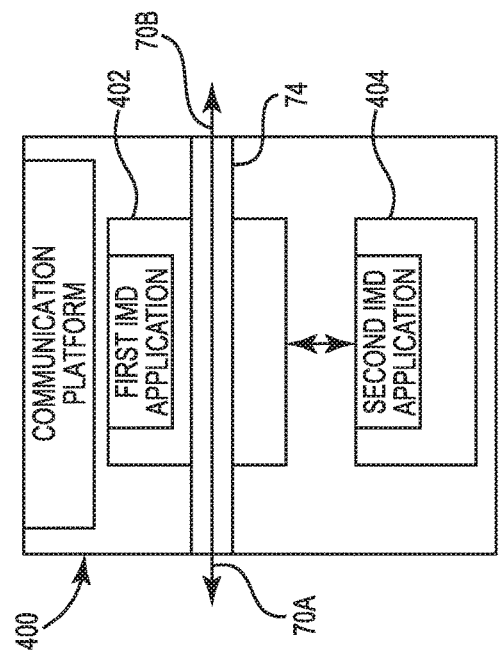

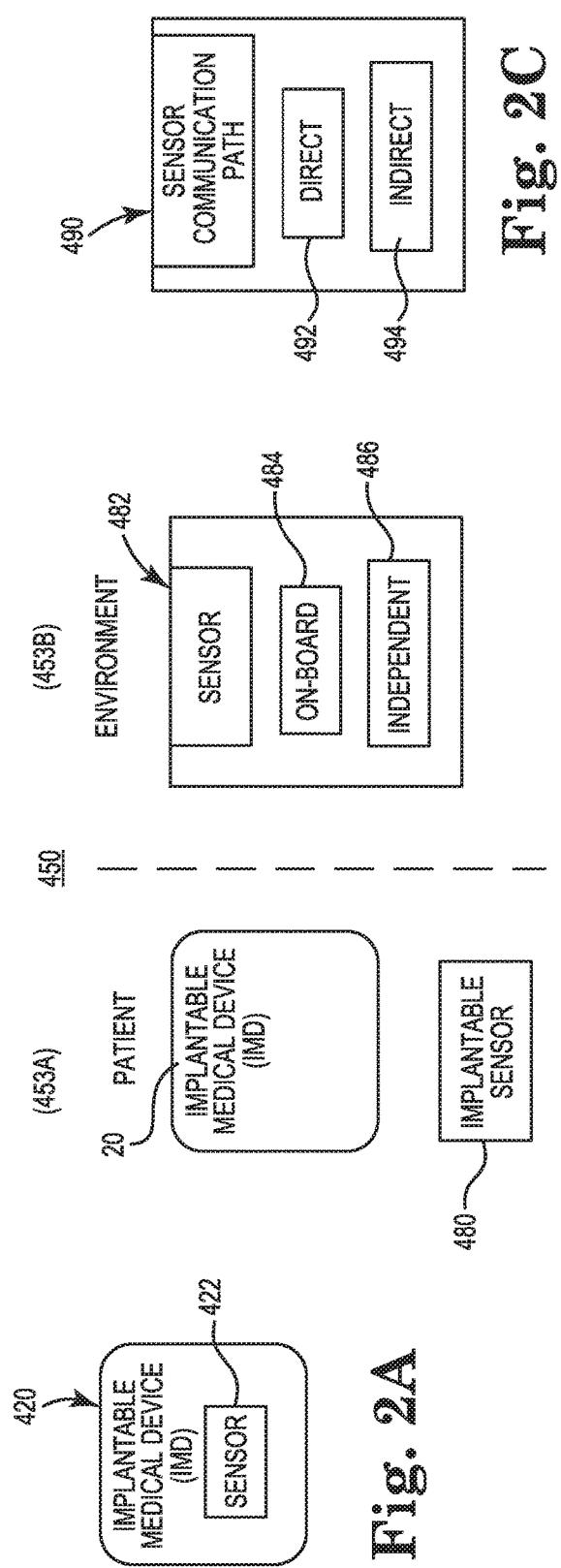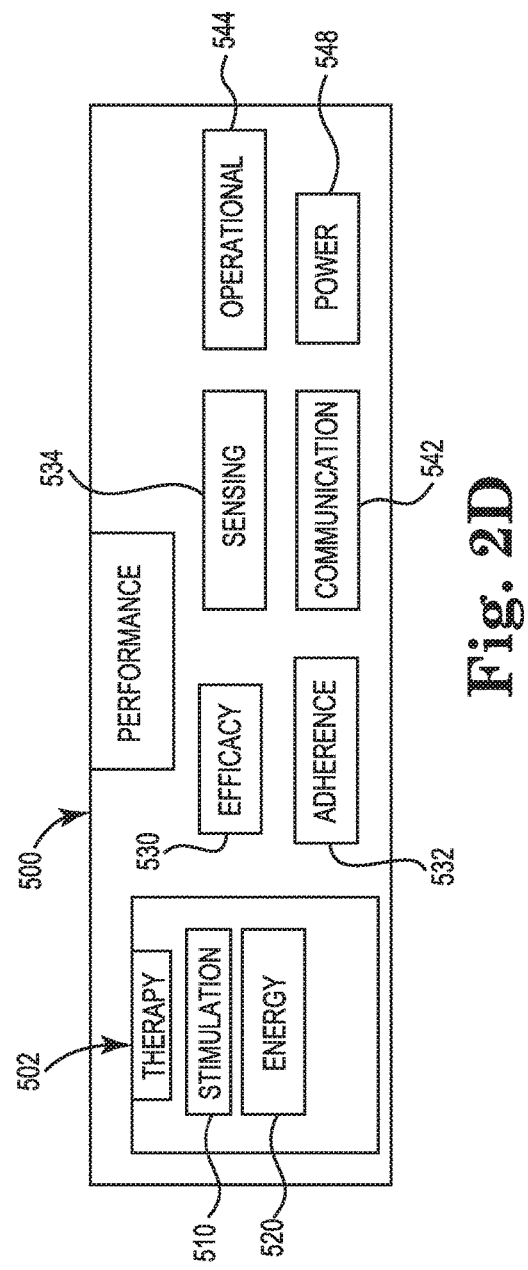

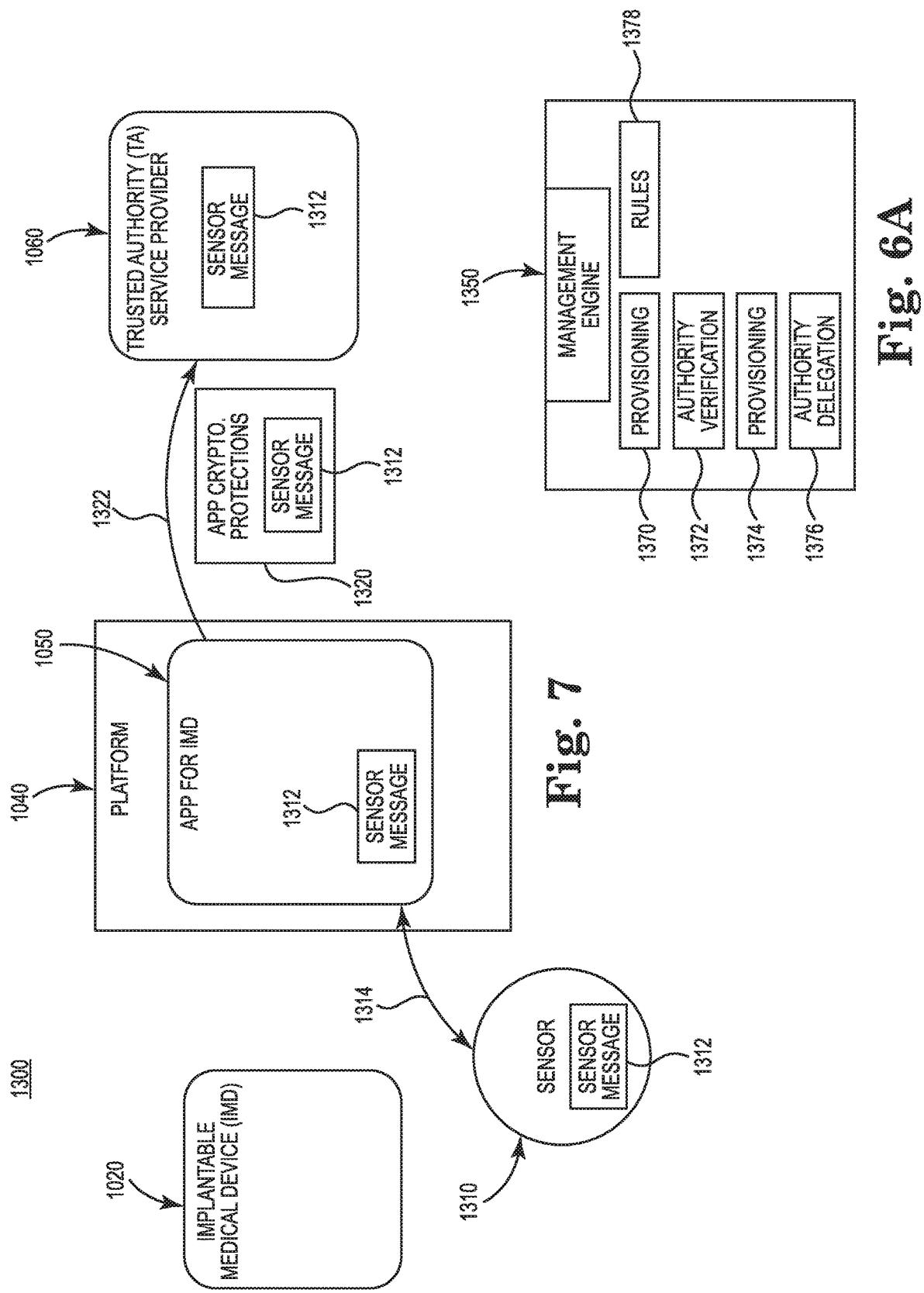

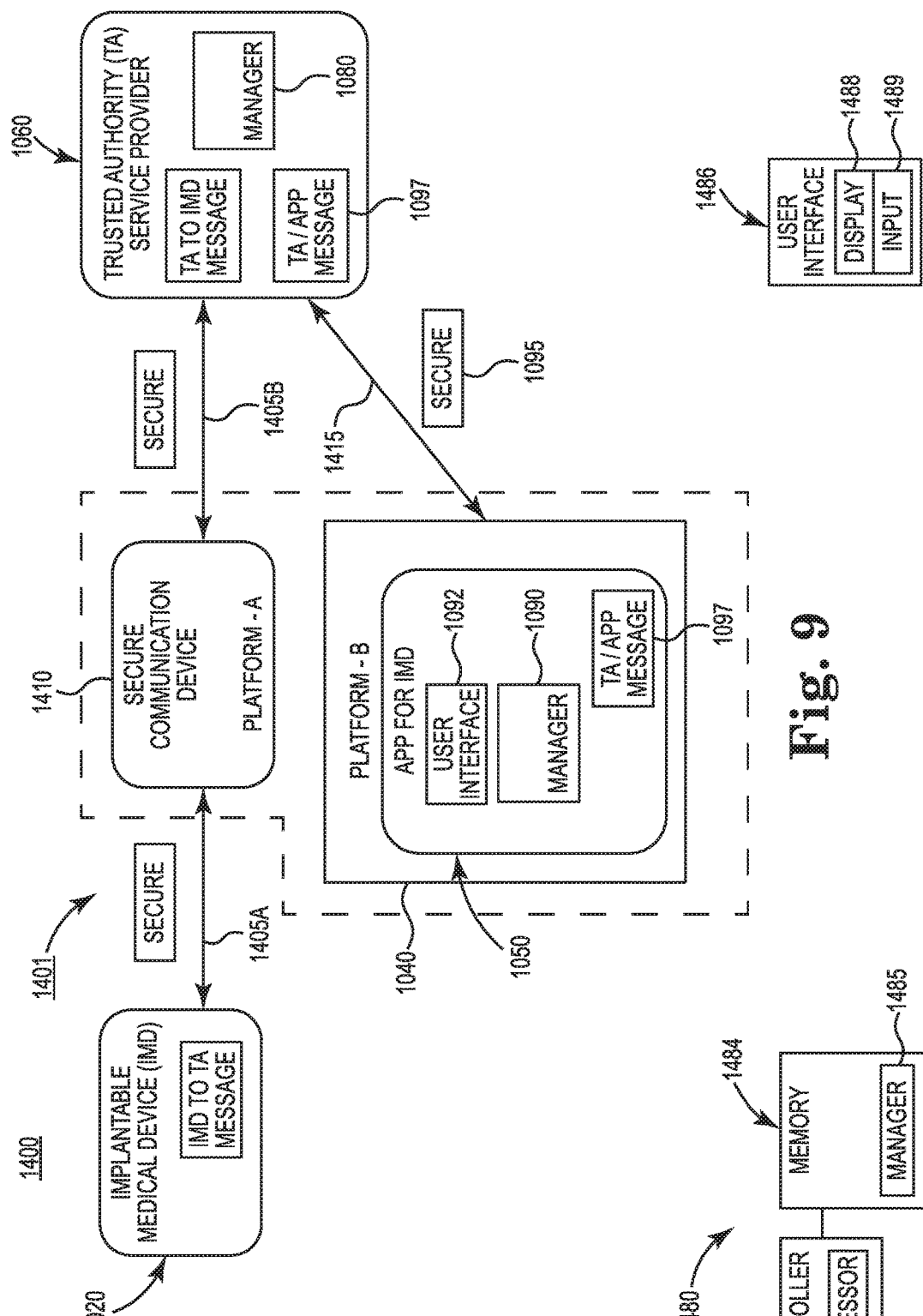
Fig. 9
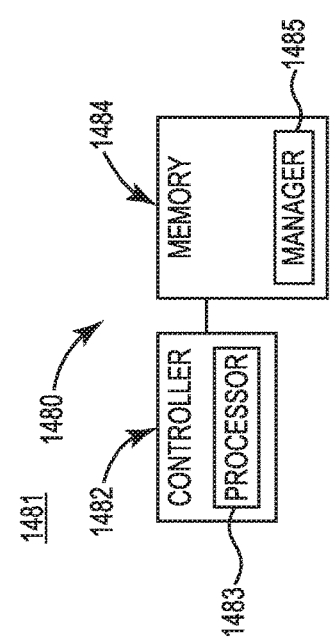
Fig. 10
Fig. 11

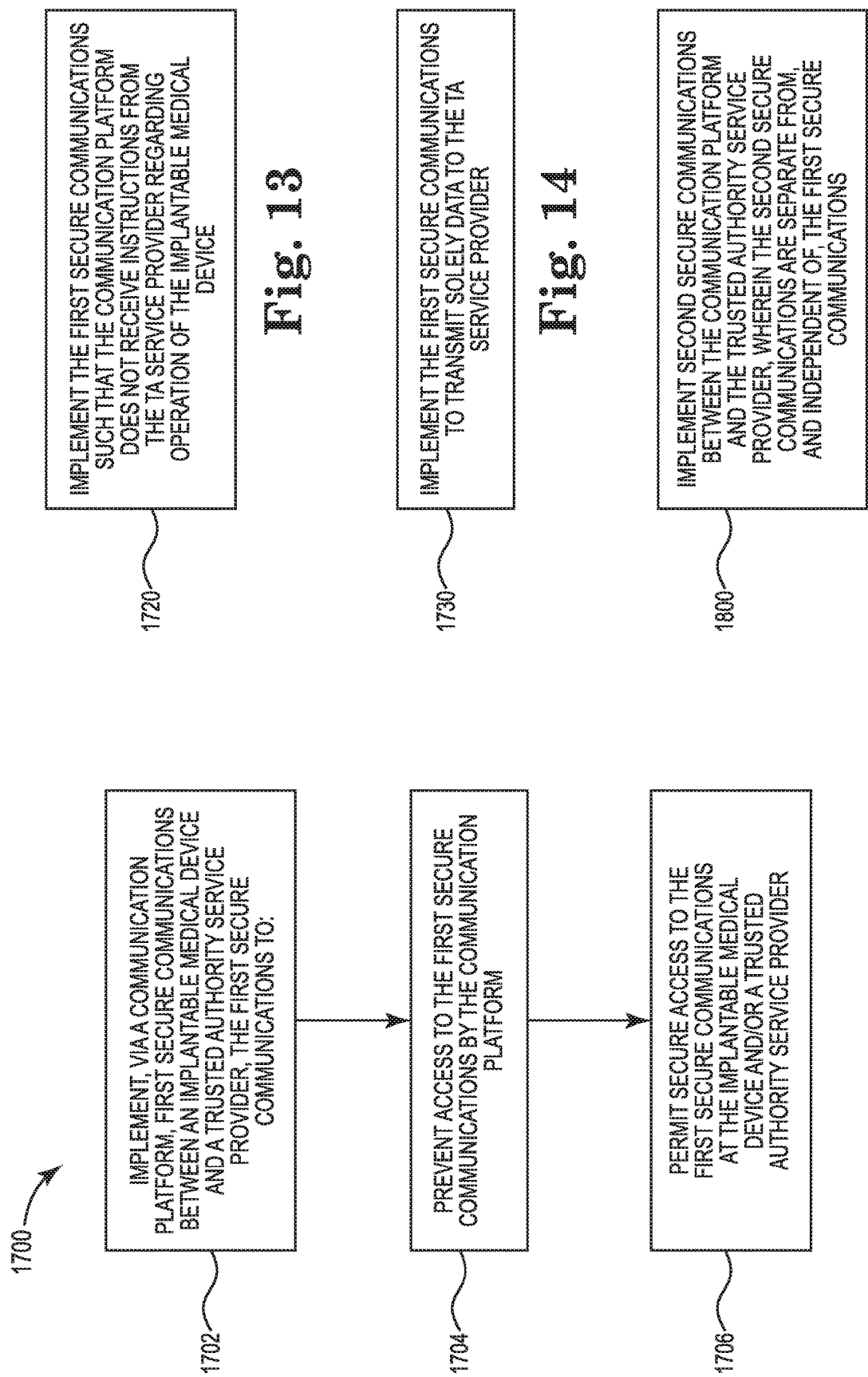

PLATFORM FOR SECURE COMMUNICATIONS WITH MEDICAL DEVICE

CROSS-REFERENCE TO RELATED APPLICATIONS

This Utility Patent Application is a U.S. National Stage filing under 35 U.S.C. § 371 of PCT/US2016/046600, filed Aug. 11, 2016, which claims benefit of U.S. Provisional Application 62/203,435, filed Aug. 11, 2015, both of which are hereby incorporated by reference.

BACKGROUND

Active implantable medical devices and the systems that interact with them are highly regulated to maintain reasonable safeguards for the patient and their caregivers. Accordingly, there has been little flexibility in the type of devices permitted for use in monitoring and/or controlling active implantable medical devices.

BRIEF DESCRIPTION OF THE DRAWINGS

FIG. 1A is a block diagram schematically representing a system including a communication platform, according to one example of the present disclosure.

FIG. 1B is a block diagram schematically representing a security mechanism, according to one example of the present disclosure.

FIG. 1C is a block diagram schematically representing a security manager, according to one example of the present disclosure.

FIG. 1D is a block diagram schematically representing a communication platform, according to one example of the present disclosure.

FIG. 1E is a block diagram schematically representing an application for an implantable medical device (IMD), according to one example of the present disclosure.

FIG. 1H is a block diagram schematically representing a system including a communication platform including an IMD application, according to one example of the present disclosure.

FIG. 1I is a block diagram schematically representing a communication platform, according to one example of the present disclosure.

FIG. 1J is a block diagram schematically representing an authentication engine, according to one example of the present disclosure.

FIG. 2A is a block diagram schematically representing an implantable medical device including a sensor, according to one example of the present disclosure.

FIG. 2B is a block diagram schematically representing an implantable medical device and a separate implantable sensor within a patient and schematically representing a sensor external to the patient, according to one example of the present disclosure.

FIG. 2C is a block diagram schematically representing a sensor communication path, according to one example of the present disclosure.

FIG. 2D is a block diagram schematically representing a performance engine, according to one example of the present disclosure.

FIG. 6A is a block diagram schematically representing a management engine, according to one example of the present disclosure.

FIG. 7 is a block diagram schematically representing a system including a communication platform, according to one example of the present disclosure.

FIG. 9 is a block diagram schematically representing a system including a communication platform, according to one example of the present disclosure.

FIG. 10 is a block diagram schematically representing a control portion, according to one example of the present disclosure.

FIG. 11 is a block diagram schematically representing a user interface, according to one example of the present disclosure.

FIG. 12 is a flow diagram schematically representing a method of implementing secure communications, according to one example of the present disclosure.

FIG. 13 is a diagram schematically representing an implementation of first secure communications, according to one example of the present disclosure.

FIG. 14 is a diagram schematically representing an implementation of first secure communications, according to one example of the present disclosure.

FIG. 15 is a diagram schematically representing an implementation of second secure communications, according to one example of the present disclosure.

DETAILED DESCRIPTION

Figure 1F:
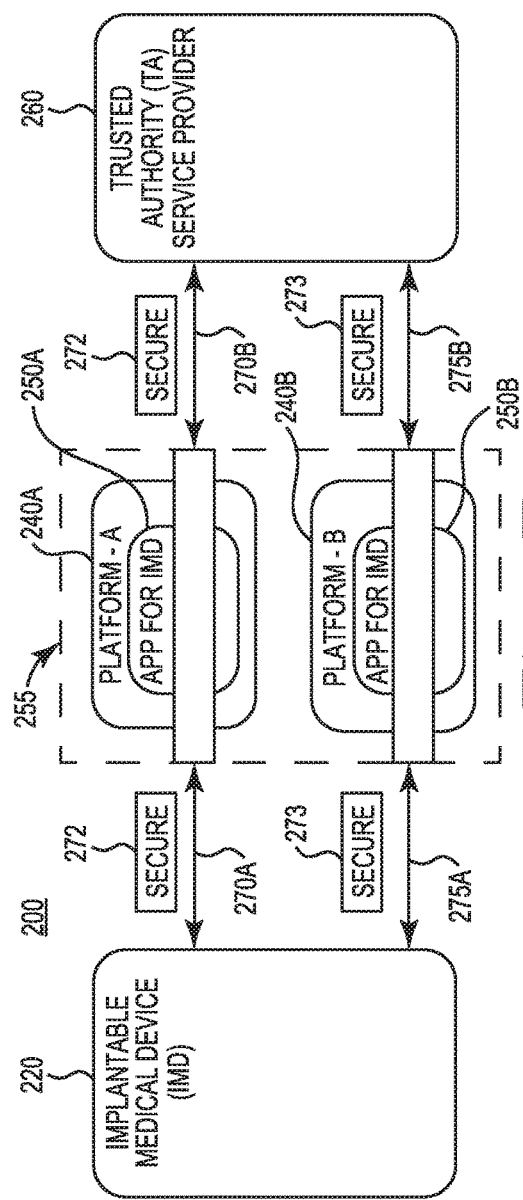
FIG. 1F is a block diagram schematically representing a system including a communication platform with multiple channels, according to one example of the present disclosure.

In the following Detailed Description, reference is made to the accompanying drawings which form a part hereof, and in which is shown by way of illustration specific examples of the present disclosure which may be practiced. It is to be understood that other examples may be utilized and structural or logical changes may be made without departing from the scope of the present disclosure. The following detailed description, therefore, is not to be taken in a limiting sense.

In at least some examples of the present disclosure, a communication platform at least partially implements first secure communications between an implantable medical device and a trusted authority service provider. In some examples, the first secure communications prevent access to at least content of the first secure communications by the communication platform. In some examples, the first secure communications are accessible at the implantable medical device and at the trusted authority service provider, and the first secure communications originate via at least one of the implantable medical device and the trusted authority service provider.

In at least some examples of the present disclosure, the communications platform may comprise a consumer communication device such as a smartphone, tablet computer, etc., and which is used to at least partially monitor and/or at least partially control an implantable medical device (IMD) within a patient. In some examples, this arrangement is implemented via a wireless communication protocol (such as but not limited to Bluetooth Low Energy (BLE)) within the communication platform in which the wireless communication protocol is reliable enough and operates at low enough power that they can be utilized for communication with at least some implantable medical devices (IMD). In some examples, the communication platform, which does not otherwise meet regulatory criteria to monitor and/or control an implantable medical device (IMD), can become equipped to at least partially monitor and/or at least partially control an implantable medical device (IMD) while complying with a medical device regulatory framework (i.e. meeting device reliability and security criteria).

In some examples, the communication platform is not dedicated for use in monitoring and/or controlling an implantable medical device (IMD). Accordingly, the communication platform may sometimes referred to as a non-IMD-dedicated communication platform. In some examples, the communication platform may comprise a consumer communication device, which may be portable or stationary. In some examples, the communication platform comprises a server. In some examples, the communication platform comprises a web server.

With this in mind, in some example arrangements, an application is executable on, and/or associated with, a communication platform to at least partially implement first secure communications between an implantable medical device (IMD) and a trusted authority (TA) service provider. The first secure communications include a security mechanism to prevent access to the first secure communications by the communication platform and by the application while permitting secure access to the first secure communications at the IMD and/or at the trusted authority service provider.

It will be understood that in at least some examples the security mechanism may involve encryption to implement the access prevention and may involve decryption to implement the secure access. In some such examples, the security mechanism includes or implements a security element which forms part of the first secure communications. In some examples, a similar arrangement may be applied for second secure communications, which are further described later.

In some examples, the trusted authority (TA) service provider at least partially manages operation of the IMD via the first secure communications. In some examples, via the TA service provider the application enables some user participation in operation of the IMD. As previously noted, in some examples the communications platform may comprise a communication device, such as but not limited to, a smartphone, a tablet computer, phablet, etc. generally available to ordinary consumers as a consumer communication device.

In some examples, by utilizing the presence of the TA service provider to perform and/or initiate communications with the IMD, security may be enhanced by implementing more sensitive aspects (e.g. aspects relating to medical safety) of the system in the trusted authority service provider, instead of implementing those more sensitive aspects in the communication platform (including an IMD application), which may be more susceptible to attacks such as reverse engineering.

Accordingly, whether embodied as a consumer communication device or other modality, at least some examples of the present disclosure enable a communication platform to act as the patient's controller for their IMD without exposing the patient to unnecessary risks and without exposing the communication platform to close medical regulatory scrutiny. Accordingly, in one aspect, these communication platforms (e.g. consumer communication device, desktop computer) retain their customary functions as a regular phone, tablet, computer etc. while also permitting user participation via an application (executable on the communication platform) to at least partially monitor and/or at least partially control an implantable medical device.

In some examples, a first IMD application executable via the communication platform may take the form of a service, such that at least a second IMD application executable via the communication platform may use the first IMD application as a means to communicate with the IMD and/or TA service provider. In some such examples, the first IMD application may act as a communication conduit while the second IMD application may provide control and/or information functions. In some such examples, the first IMD application may sometimes be referred to as a driver.

In some examples, at some of the example communication platforms can be implemented without modification to the communication platform, such as a consumer communication device. For instance, in at least some examples, such a communication platform does not involve an initial mode selection, does not involve separate operating systems, does not involve any special memory segregation, and the like in order to use the communication platform via the executable IMD application to at least partially monitor and/or at least partially control the implantable medical device (IMD).

In some examples, a communication platform comprises a non-IMD-dedicated communication platform. In some examples, the term "non-IMD-dedicated" communication platform refers to a communication platform which is not dedicated to exclusively communicate with, control and/or be controlled by an implantable medical device (IMD). Accordingly, with a communication device providing one example implementation of such a communication platform, in some examples, the term "non-IMD-dedicated communication device" refers to a device which is not dedicated to exclusively communicate with, control and/or be controlled by an implantable medical device (IMD). In some instances, the communication device may sometimes be referred to as communicating non-exclusively with the implantable medical device.

In some examples, the non-IMD-dedicated communication platform is a "non-medically-exclusive" communication platform, i.e. a communication platform not for exclusive medical use with IMD and/or not for exclusive medical use with external medical device.

In some instances, the non-IMD-dedicated communication platform is a personal communication device, which may be consumer grade, commercial grade, military grade, etc., and therefore may sometimes be referred to as a non-IMD-dedicated communication device. In some examples, the personal communication device may be a mobile communication device.

In some instances, the non-IMD-dedicated communication platform comprises a device not enabled for secured communications to/from the implantable medical device (IMD). In some instances, the non-IMD-dedicated communication platform is unsecured in at least the sense that it does not include a secure channel or pathway for receiving and sending secure communications (e.g. messages, transmissions, etc.) which originate from either an implantable medical device (IMD) or a trusted authority (TA) service provider and which pass through the non-IMD-dedicated communication platform.

Via at least some examples of the present disclosure, a manufacturer of an implantable medical device may experience reduced costs because they can omit designing and building an external device as a patient remote monitor. In some examples, a patient may experience greater ease of use because they can omit carrying an external device dedicated to monitor and/or control their implantable medical device while gaining the convenience of monitoring and/or controlling the implantable medical device via a communication platform, such as (but not limited to) their smartphone, tablet, or functionally similar communication device. In some examples, the communication platform is enabled for such use via an executable application (e.g. a mobile app in some examples) directed to at least partially monitoring and/or at least partially controlling the implantable medical device in the manner described throughout at least some examples of the present disclosure.

In some examples, via the IMD application executable via the communication platform, a patient and/or clinician may receive data obtained by a sensor and use that information to advance care of the patient. In some examples, such sensors may obtain information relating to pulse oximetry, accelerometry, audio, heart rate, images, and video, and the like. In some examples, such sensors may reside on or be accessible via the communication platform while in some examples, the sensor may be implantable. In some examples, such an implantable sensor may be incorporated within or on the implantable medical device. With such arrangements, in some examples the IMD application can integrate information from the implantable medical device (IMD) and sensed information relating to a physiologic state of the patient to thereby advance care of the patient.

These examples, and additional examples, are described in more detail in association with at least FIGS. 1A-15.

FIG. 1A is a block diagram of a system 10, according to one example of the present disclosure. As shown in FIG. 1A system 10 includes an implantable medical device (IMD) 20, a communication platform 40, and a trusted authority (TA) service provider 60.

In general terms, the communication platform 40 acts as an intermediary for the first secure communications 70A, 70B between the IMD 20 and the TA service provider 60. In some examples, the first secure communications 70A, 70B are implemented in a manner which prevents access to the first secure communications 70A, 70B by the communication platform 40 while permitting secure access to the first secure communications 70A, 70B at the IMD 20 and at the TA service provider 60.

In some examples, the communication platform 40 comprises a wireless communication element 75 to at least partially implement the first secure communications between the implantable medical device (IMD) 20 and the trusted authority (TA) service provider 60. In some examples, the wireless communication element 75 enables communication with devices and/or resources other than the IMD 20 and TA service provider 60.

In some examples, the TA service provider 60 at least partially manage operations of the IMD 20 via the first secure communications 70A, 70B with the IMD 20, as will be further described later. However, in some examples, the TA service provider 60 merely receives information from IMD 20 via first secure communications 70A, 70B without at least partially managing IMD 20.

FIG. 1B is a block diagram schematically representing a security mechanism 77. In some examples, the security mechanism 77 forms part of and/or helps to implement the first secure communications 70A, 70B. Accordingly, in some examples, the security mechanism 77 prevents access to the first communications 70A, 70B by the communication platform 40 while permitting secure access to the first secure communications 70A, 70B at the IMD 20 and at the TA service provider 60.

Figure 8:
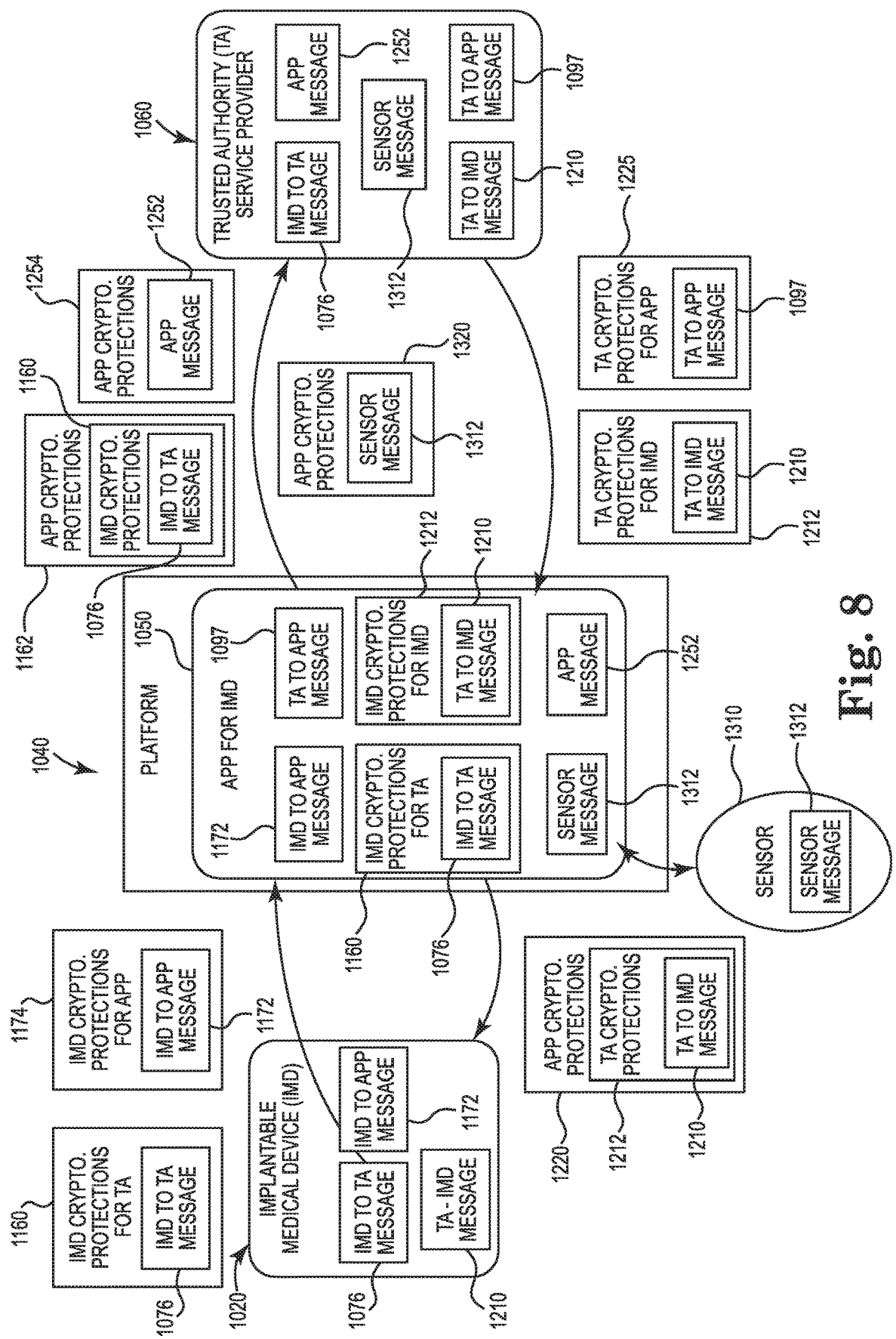
FIG. 8 is a block diagram schematically representing a system including a communication platform, according to one example of the present disclosure.

With this general arrangement of system 10 in FIG. 1A in mind, it will be understood that FIGS. 1B-11 provide more specific examples of various implementations and details regarding the operation and interaction of at least IMD 20, communication platform 40, and/or TA service provider 60. The later described FIG. 8 provides one example representation of comprehensive interactions among IMD 20, communication platform 40, and TA service provider 60, as well as other elements.

Referring again to at least FIGS. 1A-1B, in some examples, the security mechanism 77 implemented as part of the first secure communications is schematically represented via first security elements 72, as shown in FIG. 1A. Meanwhile, directional arrows 70A, 70B schematically represent first secure communications occurring between IMD 20 and trusted authority TA service provider 60. Box 74 schematically represents a manner in which the communication platform functionally provides a channel or acts as an intermediary for the first communications 70A, 70B between the IMD 20 and the TA service provider 60. In other words, element 74 does not represent a separately identifiable physical structure within the communication platform 40. It will be further understood that in some examples, at least some of which are further described later, an application associated with the communication platform 40 provides the functional channel or acts as the intermediary for the first communications 70A, 70B.

In some examples, both the TA service provider 60 and the communication platform 40 are external to the patient's body while the IMD 20 is implanted within the patient's body.

In some examples, the IMD 20 comprises a passive implantable medical device. In some examples, the IMD 20 comprises an active implantable medical device.

In some examples, one such active IMD (AIMD) 20 is an implantable neurostimulation system. In some examples, the AIMD 20 includes at least an implantable pulse generator (IPG) or other implantable neurostimulator. In some examples, the AIMD 20 includes a stimulation element operably coupled relative to the IPG. In some examples, the AIMD 20 includes an implanted respiratory sensor operably coupled relative to the IPG. In some examples, the AIMD 20 is adapted to treat obstructive sleep apnea and/or other sleep disordered breathing behavior. Is some examples, the AIMD 20 is adapted to treat diseases amenable to therapy via neurostimulation. In some examples, the AIMD 20 is adapted to treat diseases amenable to therapy via other forms of electrically, mechanical, hydrologic, chemical, genetic, and/or biological activities implementable via the AIMD 20.

In some examples, implementing communication platform 40 is not strictly dependent on all of the elements of the AIMD 20 being implanted.

In some examples, IMD 20 comprises a passive implantable medical device (PIMD) which is subject to substantially the same degree of medical regulatory criteria as IMD 20. It will be understood that in these examples, the IMD 20 would be implemented in the form of passive implantable medical device (PIMD) in at least some of the examples described throughout the present disclosure.

In some examples, instead of an implantable medical device (IMD) 20, system 10 comprises a non-implantable medical device (NIMD) 20 which has no elements implanted within the patient's body, but which otherwise is subject to substantially the same degree of medical regulatory criteria as IMD 20. The NIMD 20 can be an external fluid pump, such as for treating diabetes, or can take other forms for other purposes.

In some examples, the non-implantable medical device (NIMD) 20 comprises an active device, e.g., active non-implantable medical device (ANIMD) 20. In some examples, the non-implantable medical device comprises a passive device, e.g. passive non-implantable medical device (PNIMD) 20. With this in mind, it will be understood that in some examples the IMD 20 may be implemented in the form of an ANIMD 20 or PNIMD 20 in at least some of the examples described throughout the present disclosure.

In some examples, the IMD 20 includes a communications security manager 22 (FIG. 1C) to manage security mechanisms at the IMD 20. In some examples, the TA service provider 60 includes a communications security manager 62 (FIG. 1C) to manage security mechanisms at the TA service provider 60.

In some examples, the security mechanisms associated with the respective first and second secure communications are implemented via at least the respective security managers 22, 62, which include cryptographic technologies, and at least some of which are further described below and later illustrated in association with at least FIGS. 1A-15.

In some examples, cryptographic protection of communications within system 10 includes implementing a symmetric cryptographic protection protocol and/or an asymmetric protection protocol. In some examples, a cryptographic protection protocol for communications at least between the IMD 20 and the TA service provider 60 implements at least some aspects of both symmetric and asymmetric protection protocols. In some examples, a symmetric protection protocol includes stream and block ciphers such as, but not limited to, the Advanced Encryption Standard (AES) protocol. In some examples, an asymmetric protection scheme includes public/private key pairs such as, but not limited to, the Rivest-Shamir-Adleman (RSA) protocol.

In some examples, as further described below and throughout examples of the present disclosure, communication platform 40 comprises an implantable medical device (IMD) application 50 as shown in at least FIG. 1E. In at least some such examples, at least some of substantially the same above-described protection protocols are used to implement secure communications between the IMD application 50 and the IMD 20 and/or between the IMD application 50 and the TA service provider 60. At least some examples of the IMD application 50 are described later in association with at least FIG. 1H and throughout later examples of the present disclosure.

In some examples, the communication platform 40 comprises a user interface, such as but not limited to the user interface 1092 as later described in association with at least FIG. 3A, the user interface 600 as later described in association with at least FIG. 2E, and/or the user interface 1486 as later in association with at least FIG. 1I. In some instances, such a user interface comprises an input mechanism and a display with such user interface being implemented a corresponding graphical user interface of the communication platform 40.

It will be understood that the IMD 20 already incorporates regulatory constraints for safe, efficacious therapy and communication.

In some examples, the implantable medical device (IMD) 20 includes at least one communication element (ISM inductive communications, Bluetooth, Wi-Fi, etc.) capable of interaction with communication platform 40, which in at least some examples may be a consumer communication devices such as a smartphone, tablet, phablets, and the like. In some examples, such communication elements operates in a low power mode (e.g. Bluetooth Low Energy—BLE), which may contribute to performing secure communications by making it more difficult for others to surreptitiously intercept the communications.

In some examples, IMD 20 includes a security manager 22 (FIG. 1C) which implements cryptographic technologies capable of verifying a communication (e.g. message) as originating from the trusted authority (TA) service provider 60, verifying the validity of the contents of the communication, verifying the temporal integrity of the communication, the intended recipient of the communication, and/or keep the contents of the communication confidential (e.g. encrypted).

In some examples, the security manager 22 (FIG. 1C) associated with IMD 20 implements cryptographic technologies capable of signing a communication so that the communication can be read solely by the TA service provider 60 which can also validate the integrity of the contents of the communication, validate the temporal integrity of the communication, validate the intended recipient of the communication, and/or keep the contents of the communication confidential, such as via encryption.

In some examples, the IMD 20 implements a cryptographic protection protocol involving symmetric keys for communication with the TA service provider 60. In some examples, a first key can be used for standard secure communications. In some examples, a second key can be used solely for direct communications between the IMD 20 and the TA service provider 60 for the purpose of changing symmetric keys (such as the first key) or other security features. In some examples, each key is paired with a random bit of secret data/string (e.g. salt) to buffer data and increase security. In some examples, such an arrangement may help to mitigate replay-style attacks.

As noted elsewhere, in at least some examples the communication platform 40 may act as an intermediary which does not have access to the content of the secure communications.

In some examples, the IMD 20 includes a provisioning element for initiation of communication with the trusted authority (TA) service provider 60 via a communication platform 40, such as but not limited to a consumer communication device (e.g. a non-IMD-dedicated device).

In some examples, the IMD 20 includes a protective mechanism to mitigate an attack intended to deplete a power source of the IMD 20. In one such example, the IMD 20 utilizes ultra-low-power communications or communications that are self-powered (e.g. NFC, RFID, inductive) such that the IMD 20 may be resistant to an attack of repeated communications aimed at depleting the power source. This arrangement is just one of several example mechanisms within the present disclosure which provide a layered approach to secure an environment to enable at least partially controlling an IMD 20 via an IMD application (e.g. at least 50 in FIG. 1E, 1050 in FIG. 3A) executable via communication platform 40.

In some examples, another layer of protection includes the IMD 20 evaluating each external communication device attempting to communicate with the IMD 20. For instance, the IMD 20 may evaluate a Bluetooth/MAC address along with device data and credentials in the communication packets from the external communication device. If the external communication device is not an authorized communication device according to the IMD 20, then the IMD 20 disregards future communications from that external communication device and that MAC address for a certain period of time. In some examples, such evaluation is incorporated within the IMD security manager 22 (FIG. 1C).

In some examples, multiple layers of the protection mechanisms described above (regarding protecting a power source of the IMD 20) are implemented in combination.

In some examples, the communication platform 40 comprises an application 50 as shown in FIG. 1E for interaction with IMD 20, which may sometimes be referred to as an IMD application 50. Several examples of the IMD application 50 are described throughout various examples of the present disclosure are described in association with at least 1H-15.

FIG. 1D is a block diagram schematically representing a communication platform 140, according to one example of the present disclosure. In some examples, the communication platform 140 comprises at least some of substantially the same features and attributes as communication platform 40 as described in association with at least FIGS. 1A-1C. In some examples, the communication platform 140 comprises at least some of substantially the same features as communication platform 240A, 240B, 1040 as described throughout examples of the present disclosure.

In some examples, the communication platform 140 provides at least some example implementations of the communication platform 40 in FIG. 1A and of the various communication platforms as described throughout the examples of the present disclosure.

In general terms, the communication platform 140 comprises some combination of hardware and applications executable via such hardware to facilitate first secure communications 70A, 70B to pass through communication platform 40 in the manner described throughout the examples of the present disclosure. Accordingly, a wide variety of types of devices, types of applications, etc. may be used to implement communication platform 140 and to implement secure communications through communication platform 140.

With this in mind, as shown in FIG. 1D, in some examples the communication platform 140 comprises a mobile device 142, which has at least wireless communication capabilities suitable for communicating with IMD 20 and having wired and/or wireless communication capabilities suitable for communicating with TA service provider 60. In some examples, the mobile device 142 is a handheld device. In some examples, the mobile device 142 is not typically handheld but is otherwise readily portable. As further described in greater detail throughout various examples of the present disclosure, in some examples the mobile device 142 may comprise a consumer communication device, such as a smart phone, tablet, phablet, notebook computer, etc. In some examples, mobile device 142 comprises a non-IMD-dedicated mobile device.

In some examples, the communication platform 140 comprises a stationary device 144. In some examples, the stationary device 144 comprises a web server. However, it will be understood that in some examples, the web server can be sized to be portable or mobile. In some examples, the stationary device 144 comprises a desktop computer.

In some examples, the communication platform 140 comprises a combination of a stationary device 144 and a dongle 146 with dongle 146 having at least wireless communication capabilities suitable for communicating with IMD 20. The dongle 146 and stationary device 144 may communicate together via wired or wireless pathways, while stationary device 144 may communicate with the TA service provider via wired or wireless pathways. In some examples, the dongle 146 may be used with non-stationary computers as part of communication platform 140.

As further shown in FIG. 1D, in some examples, the communication platform 140 incorporates a cloud resource 161 by which a mobile device 142 or stationary device 144 utilizes the cloud resource 161 to at least partially implement first secure communications 70A, 70B. In some examples, cloud resource 161 can host an IMD application 50 (FIG. 1H), which can be accessed and then executed on communication platform 40, such as a mobile device 142, stationary device 144, etc.

In some examples, the communication platform 140 comprises more than one component arranged in series 163 or may comprise more than one component arranged in parallel 165.

In some examples, the communication platform 140 is not dedicated for exclusive communication with an implantable medical device (IMD) and therefore may sometimes be referred to as a non-IMD-dedicated communication platform 171, which may comprise a non-IMD-dedicated device. In contrast, at least some commercially available devices for communication with an implanted medical device are tailored for communication exclusively with the implanted medical device, such as a dedicated patient programmer (e.g. dedicated remote control).

In some examples of the present disclosure, the communication platform 140 is dedicated for communication with one implantable medical device (IMD) but is not necessarily dedicated to use for a particular brand/model of implantable medical device. In such examples, the platform 140 may sometimes be referred to as a non-specific-IMD-dedicated communication platform 173, which may comprise a non-specific-IMD-dedicated device.

In some examples, the communication platform 140 is dedicated for communication with several different implantable medical devices (IMDs). In some examples, the different implantable medical devices may all be the same brand (i.e. a common manufacturer). However, in some examples, at least some of the different implantable medical devices may comprise different brands. In such examples, the platform 140 may sometimes be referred to as a multi-IMDdedicated communication platform 175 as shown in FIG. 1D, which may include a multi-IMD-dedicated device.

FIG. 1F is a block diagram schematically representing a system 200, according to one example of the present disclosure. As shown in FIG. 1F, system includes an implantable medical device (IMD 220), communication platform 240A, 240B, and TA service provider 260, which have at least some of substantially the same features and attributes as the analogous components 20, 40, 60 in system 10 as described in association with at least FIGS. 1A-1E. However, in some examples, the communication platform in system 200 is implemented as at least two separate portions 240A, 240B, each of which comprise a separate IMD application 250A, 250B.

As shown in FIG. 1F, first platform portion 240A facilitates a first component of 270A, 270B of first secure communications between IMD 220 and TA service provider 260 in cooperation with security mechanism 272 (e.g. security elements 272), while second platform portion 250A facilitates a second component 275A, 275B of first secure communications between IMD 220 and TA service provider 260 in cooperation with security mechanism 273 (e.g. security elements 273). In some instances, these different pathways may sometimes be referred to as a two different channels, such as first channel and a second channel.

In some examples, the first channel is arranged to implement first secure communications according to a first level of access privileges to a content of the first secure communications. Meanwhile, the second channel is arranged to implement the second secure communications according to a second level of access privileges to the content of the first secure communications, wherein the second level of access privileges is different than the first level of access privileges.

In some examples, the first channel (e.g. Platform A) may be dedicated to a patient application and the second channel (e.g. Platform B) may be dedicated to a clinician application. In this arrangement, the clinician application has full privileges while the patient application has whatever limited privileges are granted by the clinician.

In some examples, the first channel (e.g. Platform A) may be dedicated to a patient application and the second channel (e.g. Platform B) may be dedicated to a home monitor application, which is granted read-only access to IMD.

In some examples, one channel may be dedicated to a clinician with full privileges while the other channel has less privileges such as a caregiver application with a displayable subset of read-only IMD information or such as an emergency use application to disable therapy only in an emergency situation.

The two platform portions 240A, 240B are separate from, and independent of, each other. In some examples, the two IMD applications 250A, 250B are separate from, and independent of, each other. However, in some examples, the two IMD applications 250A, 250B represent distributed portions of a single IMD application.

In some examples, the two separate platform portions 240A, 240B are embodied in a single housing 255.

Figure 1G:
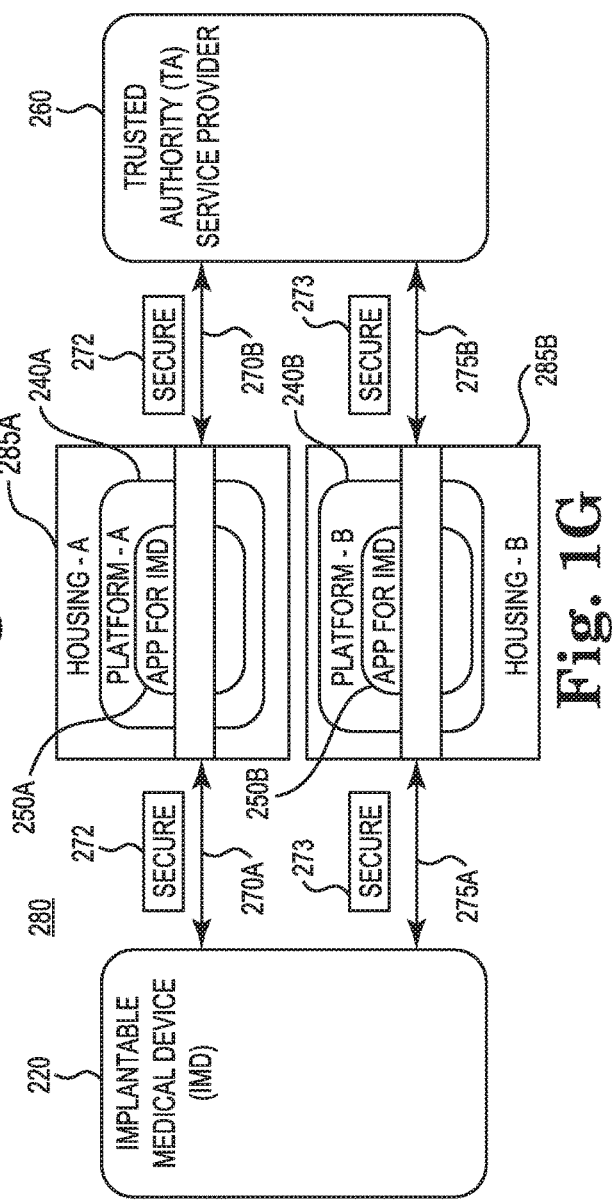
FIG. 1G is a block diagram schematically representing a system including a communication platform with multiple channels, according to one example of the present disclosure.

FIG. 1G is a block diagram schematically representing a system 280, according to one example of the present disclosure. System 280 comprises substantially the same features and attributes as system 200 in FIG. 1F, except with a first platform portion 240A (and IMD application 250A) implemented in a first housing 285A and with a second platform portion 240B (and IMD application 250B) implemented in a second housing 285B. First housing 285A is separate from, and independent of second housing 285B.

FIG. 1H is a block diagram schematically representing a system 380, according to one example of the present disclosure. In some examples, system 300 comprises at least some of substantially the same features and attributes as systems 10, 200, 280 as previously described in association with at least FIGS. 1A-1G, except further including IMD application 50 and second secure communications 394 via second security mechanism 395 (e.g. security elements 395).

In some examples, via execution by communication platform 40, the IMD application 50 (FIG. 1E) may wirelessly transmit communications to the IMD 20 or to the TA service provider 60 via a security mechanism, which provides an additional layer of security on top of the security mechanisms already present for communications originating from the TA service provider 60 or originating from the IMD 20, respectively. In one aspect, this arrangement provides a layered security approach by which multiple layers of security act to protect communications from the TA service provider 60 to the IMD 20 or from the IMD 20 to the TA service provider 60. In some examples, the layer of security provided via IMD application 50 (as executable via communication platform 40) may enable the TA service provider 60 to delegate some responsibilities to the IMD application 50 regarding the implementation of secure communications.

In some examples, the arrangement of IMD application 50 adding a layer of security (onto communications already secured by the IMD 20 and/or the TA service provider 60) helps to support verification of the IMD application 50 from communication session-to-communication session in support of a loose pairing concept mediated by the TA service provider 60. For instance, the TA service provider 60 may authorize an IMD application 50 (executable on a communication platform 40) to communicate with an IMD 20 in an arrangement such that the TA service provider 60 can use a signature of that particular IMD application 50 instance on that particular communication platform 40 to actively monitor and secure the communication path to the IMD 20. The IMD application 50 is loosely paired to the IMD 20 and the communication platform 40 may already typically include a method to validate a user via a user ID (e.g. via Microsoft ID, Google ID, or Apple ID). In some examples, the TA service provider 60 may further validate the user via such methods to help confirm continued authorization of the user, communication platform 40, and IMD application 50 to interact with the IMD 20. With this arrangement, in some examples, if the communication platform 40 becomes associated with a different user ID, then the IMD application 50 and/or TA service provider 60 may take additional steps to verify the user prior to allowing access. It will be understood that in some examples, this arrangement may be applicable for clinicians as well in which a "user ID" is used to further validate access by a clinician. Moreover, in some examples, a clinician may be validated access via a "user ID" at TA service provider 60 for multiple IMDs 20 and/or a IMD application 50 for multiple IMDs 20, whether the multiple IMDs 20 are associated with one patient or each of the multiple IMDs 20 are associated with a different patient.

As shown in FIG. 1H, in some examples, IMD application 50 at least partially manages operations of the IMD 20 via second secure communications 394 from the IMD application 50 to the TA service provider 60. In one aspect, in response to the second communications 394, the TA service provider 60 forms at least a portion of the first communications 70A, 70B to be transmitted through the communication platform 40 (and IMD application 50) to the IMD 20.

As shown in FIG. 1H, in some examples, the IMD application 50 at least partially monitors operations of the IMD 20 via second communications 394 from the TA service provider to the IMD application 50. In one aspect, the second communications 394 are at least partially based on the first communications 70A, 70B between the IMD 20 and the TA service provider 60.

FIG. 1I is a block diagram schematically representing a communication platform, according to one example of the present disclosure. In some examples, communication platform 400 comprises at least some of substantially the same features and attributes as communication platform 20, 140 associated with FIGS. 1A-1H), except with IMD application 50 implemented in an at least partially distributed arrangement. In particular, as shown in FIG. 1I, in some examples, the communication platform 400 comprises a first IMD application 402 executable via the communication platform. In some examples, the first IMD application 402 may sometimes be referred to as a service. A second IMD application 404 executable via (and/or associated with) the communication platform 400 may use the first IMD application 402 to communicate with the IMD 20 and/or TA service provider 60. In some such examples, the first IMD application 402 may act as a communication conduit while the second IMD application 404 may provide at least some operational functionality, information functionality, performance functionality, security functionality, etc. for IMD 20 and/or in association with TA service provider 60 and consistent with such functionalities as described throughout at least some examples of the present disclosure. In some examples, the first IMD application 402 may sometimes be referred to as a driver.

FIG. 1J is a block diagram schematically representing an authentication engine 350, according to one example of the present disclosure. In some examples, prior to communication with the IMD 20, an additional layer is security is implemented via an authentication engine 350 in addition to the security implemented via the first or second secure communications (as described throughout at least some examples of the present disclosure). In some examples, this additional authentication may be implemented at an initial pairing between the IMD 20 and a communication partner (e.g. TA service provider 60, communication platform 40, IMD application 50) while in some examples, the additional authentication is implemented each time that a communication with IMD 20 is to occur.

In some examples, at least a portion of the authentication engine 350 may be implemented as part of IMD 20 while in some examples, at least a portion of the authentication engine 350 may be implemented as part of IMD application 50 and/or TA service provider 60. In some examples, at least a portion of authentication engine 350 may be implemented via communication platform 40.

As shown in FIG. 1J, in some examples authentication engine 350 comprises a two-step authentication function 352 to implement a second step of authentication in addition to whatever initial authentication was implemented via the first secure communications. In some examples, a second step of authentication may be implemented via a user id function 354, a biometric function 356, a physical function 358, and/or a messaging function 360. However, it will be understood that the functions 354-360 are representative such that in some examples other types of second step authentication are not excluded for implementing a second step authentication via engine 350.

The user id function 354 calls for a user identification (user id) for the second step authentication, which is managed by a third party and/or the TA service provider 60. The user id function 354 also may call for an associated password. In some examples, to implement a second step authentication, the biometric function 356 of authentication engine 350 calls for the user to present a recognizable physiologic feature, such as a fingerprint, retina, etc. for scanning or sensing. In some examples, to implement a second step authentication, the physical function 358 of authentication engine 350 calls for physical information, such as an activation code associated with the IMD 20. In some examples, In some examples, to implement a second step authentication, the messaging function 360 of authentication engine 350 calls for a message, such as an a short message system (SMS; e.g. text) or other phone messaging tool. In some examples, a combination or hybrid of the various functions 354-360 are implemented to achieve a two-step authentication via engine 350.

FIG. 2A is a block diagram schematically representing an implantable medical device (IMD) 420, according to one example of the present disclosure. In some examples, IMD 420 comprises at least some of substantially the same features and attributes as IMD 20 as previously described in association with at least FIGS. 1A-1H, except further comprising an on-board sensor 422 as shown in FIG. 2A. The on-board sensor 422 is provided to sense physiologic-related information regarding the patient. This sensed information is at least tracked via the implantable medical device (IMD) 420 and in some instances may be communicated to TA service provider 60 (FIG. 1A) and/or IMD application 50 (FIGS. 1E, 1H).

FIG. 2B is a block diagram 450 schematically representing various sensor arrangements associated with an implantable medical device (IMD) 20, according to one example of the present disclosure. In some examples, IMD 20 comprises at least some of substantially the same features and attributes as IMD 20 as previously described in association with at least FIGS. 1A-1H.

As shown in FIG. 2B, an implantable sensor 480 is provided to sense physiologic-related information regarding the patient. The implantable sensor 480 is external to the implantable medical device 20, but implantable within the patient's body (453A). In some examples, the implantable sensor 480 has a direct communication link 492 (FIG. 2C) to the implantable medical device (IMD) 20 to directly provide sensed information to IMD 20.

However, in some examples, the implantable sensor 480 has an indirect communication link 494 (FIG. 2C) or path to the implantable medical device (IMD) 20 to provide sensed information to IMD 20. In some such examples, the sensed information is not directly communicated to the IMD 20 and instead is first communicated to TA service provider 60, communication platform 40, IMD application 50, and/or other destinations. In some examples, the element which receives such sensed information may selectively communicate the sensed information (or portions thereof) to the IMD 20.

As further shown in FIG. 2B, in some examples one arrangement associated with implantable medical device (IMD) 20 may comprise a sensor 482 external to the patient 453A, and as such may sometimes be referred to as a sensor 482 within the environment 453B external to the patient 453A. In some examples, the sensor 482 comprises an on-board sensor 484, such that the sensor is on-board a host device, such as a first portion of the communication platform 40. As one non-limiting example, the communication platform 40 can be a mobile phone (or tablet, phablet, etc.) and sensor 482 comprises a sensor which is already on-board the mobile phone, such as an accelerometer or an acoustic sensing element.

In some examples, the sensor 482 comprises an independent sensor 486, such that the sensor is separate from, and independent of, the communication platform 40 and/or TA service provider 60. In some such examples, the sensor 486 may be removably coupled relative to the patient's body. In some such examples, the sensor 486 may be physically spaced apart from the patient's body. In some examples, such sensors 486 have a direct communication link 492 (FIG. 2C) to a communication platform 40, IMD 20, and/or TA service provider 60 while in some examples, such sensors 486 may have an indirect communication link or path 494 (FIG. 2C) to the recipient, such as communication platform 40, IMD 20, and/or TA service provider 60.

The information sensed via sensors 480 and/or 482 is at least tracked and/or recorded, and in some instances may be communicated to TA service provider 60 (FIG. 1A) and/or IMD application 50 (FIGS. 1E, 1H). The tracking and/or recording may be performed via implantable medical device 20, the sensing components themselves, a communication platform 40, and/or TA service provider 60 (FIG. 1A).

In some examples, a non-implantable sensor such as sensors 484, 486 (FIG. 2A) may comprise a pulse oximetry sensor, a respiratory sensor, an accelerometer, an audio sensor, a video sensor, an EKG sensor, and the like to ascertain physiologic information to advance care of the patient.

In some examples, an implantable sensor such as sensor 422 (FIG. 2A) or sensor 480 (FIG. 2B) may comprise a respiratory sensor, an accelerometer, cardiac sensor, etc. Whether implantable or not, at least some sensors such as an accelerometer may sense a patient's activity, posture, position, etc.

FIG. 2D is a block diagram of a performance engine 500, according to one example of the present disclosure. In some examples, the performance engine 500 implements tracking, recording, and/or reporting various types of performance information related to at least an implantable medical device (IMD) 20. In some examples, the performance engine 500 may additionally at least partially implement or control operations of the IMD 20 and/or associated elements. In some examples, at least some aspects of the performance engine 500 may be implemented in IMD 20.

In some examples, at least some aspects of the performance engine 500 may be implemented in at least the TA service provider 60 and/or via the communication platform 40, such as but not limited to, in the IMD application 50.

As shown in FIG. 2D, in some examples the performance engine 500 comprises a therapy engine 502 to at least partially monitor and/or at least partially implement therapy for the patient via the IMD 20 and/or with ancillary devices. In some examples, the therapy engine 502 comprises a stimulation function 510 to control and/or monitor stimulation parameters as part of implementing neurostimulation therapy. In some examples, the therapy engine 502 comprises an energy function 520 to control and/or monitor energy usage and efficiency associated with the IMD 20.

As further shown in FIG. 2D, in some examples, the performance engine 500 comprises an efficacy function 530 to track a relative or absolute efficacy (e.g. effectiveness) of therapy for the patient. As further shown in FIG. 2D, in some examples, the performance engine 500 comprises an adherence function 532 to track adherence information regarding whether, and how, the patient is adhering to their therapeutic regimen in using IMD 20.

As further shown in FIG. 2D, in some examples, the performance engine 500 comprises a sensing function 534 to at least partially control sensing activity and/or monitor sensed information. In some examples, the sensed information originates from sensor(s) at IMD 20 and/or from sensors independent of the IMD 20, such as at least one of the sensor(s) as previously described in association with at least FIGS. 2A-2C.

As further shown in FIG. 2D, in some examples, the performance engine 500 comprises a communication function 542 to monitor and/or at least partially implement communication among the IMD 20, communication platform 40, and/or TA service provider 60.

As further shown in FIG. 2D, in some examples, the performance engine 500 comprises an operational function 544 to monitor and/or at least partially implement operational functions and parameters associated with the IMD 20. In some examples, the operational function 544 relates to all of the engines, functions, and/or parameters of the IMD 20 while in some examples, the operational function 544 relates to just some of the engines, functions, and/or parameters of the IMD 20.

In some examples, the performance engine 500 comprises a power function 548 to monitor and/or at least partially implement power functionality associated with operation of IMD 20. Such monitoring may include tracking longevity of a power source and such implementing may include selective power conservation in cooperation with the various functions of IMD 20 impacting the power supply of IMD 20. It will be understood that the power function 548 may relate to a battery but is not strictly limited to battery, such as currently commercially available batteries, but may include other types of power sources suitable for use in IMD 20. The batteries and/or other power sources may be rechargeable in some examples.

In some examples, various combinations of the engines 502 and functions 510, 520, 530, 532, 534, 542, 544, 548 of performance engine 500 operate in a complementary or cooperative manner.

In some examples, the performance engine 500 is implemented in the form of a patient performance manager 1090 in IMD application 50 and/or as a master performance manager 1080 in TA service provider 60, as later described in association with at least FIG. 3.

Figure 2E:
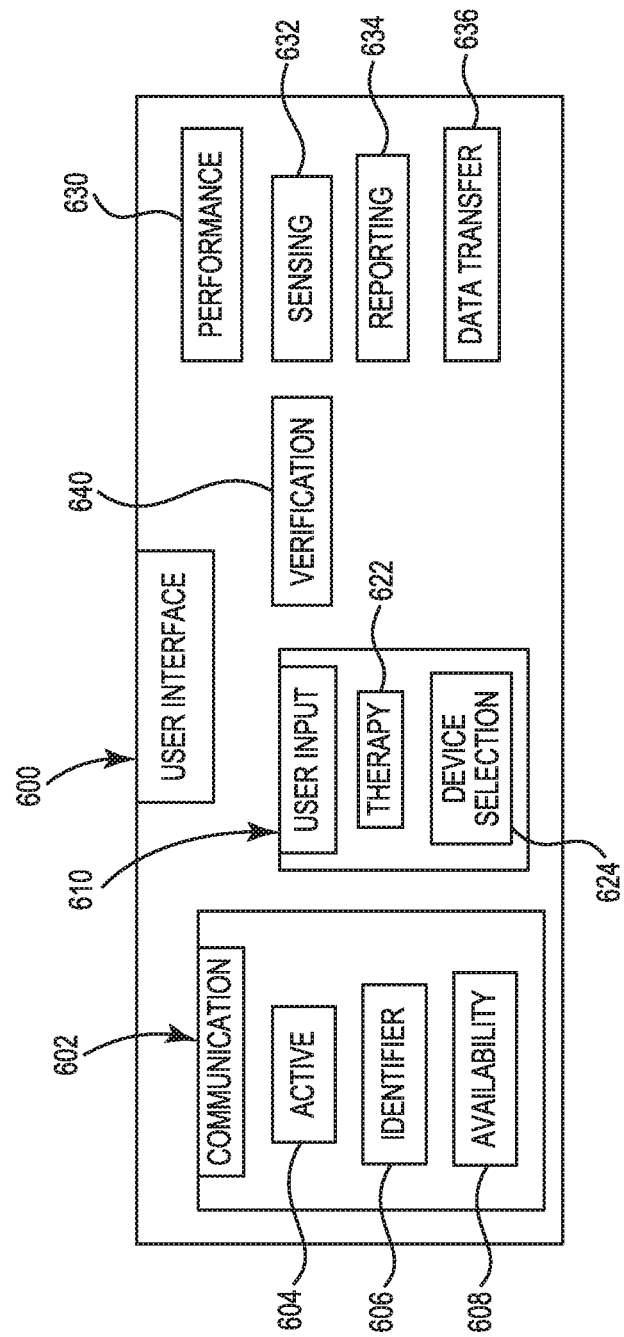
FIG. 2E is a block diagram schematically representing a user interface, according to one example of the present disclosure.

In some examples, operation of and/or monitoring the performance engine 500 may be at least partially implemented via a user interface, such as user interface 600 in FIG. 2E. In some examples, the user interface 600 is at least partially implemented via at least one of communication platform 40, including IMD application 50, and/or TA service provider 60. In some examples, user interface 600 comprises at least some of substantially the same features and attributes as user interface 1092 in FIG. 3 and/or user interface 1486 in FIG. 11. In addition, in some examples, at least some aspects of user interface 600 may be incorporated into user interface 1092 in FIG. 3 and/or user interface 1486 in FIG. 11.

As shown in FIG. 2E, in some examples, user interface 600 comprises a communication engine 602. In some examples, in general terms the communication engine 602 operates to at least partially monitor and/or at least partially implement various communication links associated with communication among IMD 20, communication platform 40, IMD application 50, and/or TA service provider 60. In some examples, the communication engine 602 may comprise an active link function 604, a link identifier function 606, and/or a link availability function 608.

In some examples, the active link function 604 monitors and/or displays which communication links are active, e.g. properly functioning, among at least the IMD 20, communication platform 40, IMD application 50, and TA service provider 60. Via such display, a patient or clinician can quickly be assured of proper communication, and therefore proper operation of the IMD 20 and related components. Alternatively, in the event that one of the communication links were not active, the patient and/or clinician would become aware of the inactive link. In some examples, in the event of an inactive link, the active link function 604 cooperates with reporting function 634 of user interface 600 to provide an alert or notification to the patient or clinician. Such reporting may in the form of an email, text (e.g. SMS), audio indicator (e.g. ringtone, other), visual indicator, etc., such as via communication platform 40, IMD application 50, and/or TA service provider 60. In some examples, such reports may indicate actions which may be taken to fix or improve operation of a particular communication link.

In some examples, the link identifier function 606 cooperates with the active link function 604 to track and/or indicate each link separately to enable a quick and effective identification of the various communication links.

In some examples, the availability function 608 tracks and/or displays a type and number of which links are available for communication with or among at least IMD 20, communication platform 40, IMD application 50, and/or TA service provider 60.

In some examples, the user interface 600 comprises a verification function 640 to verify various functions associated with operation of at least the IMD application 1050, at least some of which are further described later in association with IMD application 1050. By doing so, a clinician and/or user may use the IMD 20 with confidence and safely to advance the care of the patient. In some examples, the verification function 640 may be implemented as part of (and/or cooperate with) at least the performance engine 500 (FIG. 2D) and/or the various functions, engines, mechanisms 602, 610, 630, 632, 634, 636 of user interface 600 in FIG. 2E.

In some examples, user interface 600 comprises a user input engine 610. In some examples, in general terms the user input engine 610 may receive user input to operate user interface 600 and/or the engines and functions of IMD 20, communication platform 40, IMD application 50, and/or TA service provider 60 as appropriate to the level of access granted to the particular user (e.g. patient, clinician, technical support, etc.) for a particular aspect (e.g. 20, 40, 50, 60) of a system. In some examples, the user input engine 610 includes a therapy function 622 to at least partially monitor and/or at least partially implement at least some aspects of therapy via IMD 20.

In some examples, the user input engine 610 includes a device selection function 624 for user selection of which device or component of a system to which a user input should be applied and/or which device or component is to be monitored.

In some examples, user interface 600 comprises a performance function 630 to select displayable information regarding, and/or implement control associated with, at least some aspects of performance regarding IMD 20, communication platform 40, IMD application 50, and/or TA service provider 60. In some examples, the performance function 630 enables selective display of information and/or implementing control relating to at least some of the aspects of performance engine 500 as previously described in association with at least FIG. 2D.

In some examples, user interface 600 comprises a sensing function 632 to select displayable information regarding, and/or implement control associated with, at least some aspects of sensing in relation to IMD 20, communication platform 40, IMD application 50, and/or TA service provider 60. In some examples, the sensing function 632 enables selective display of information and/or implementing control relating to at least some of the aspects of the sensor(s) as previously described in association with at least FIGS. 2A-2C.

In some examples, user interface 600 comprises a reporting function 634 to select displayable information regarding, and/or implement control associated with, at least some aspects of reporting in relation to IMD 20, communication platform 40, IMD application 50, and/or TA service provider 60.

In some examples, user interface 600 comprises a data transfer function 634 to select displayable information regarding, and/or implement control associated with, at least some aspects of data transfer in relation to IMD 20, communication platform 40, IMD application 50, and/or TA service provider 60. In some such examples, the data transfer function 634 facilitates availability of directly downloadable information by other resources, which can be selectively communicatively coupled relative to IMD 20, communication platform 40, IMD application 50, and/or TA service provider 60

In some examples, data may be transferred on an application-to-application basis, such as IMD application 50 transferring data to another application (e.g. a commercially available application or custom application) for analysis. Such "other" applications may include applications such as, but not limited to, an Apple® healthkit application, Twitter®, etc. In this way, the data transfer function 634 may contribute to establishing a comprehensive health platform for the patient.

In some examples, various combinations of the engines 602 and functions 604, 606, 608, 610, 622, 624, 630, 632, 634, 636 in user interface 600 operate in a complementary or cooperative manner.

Figure 3:
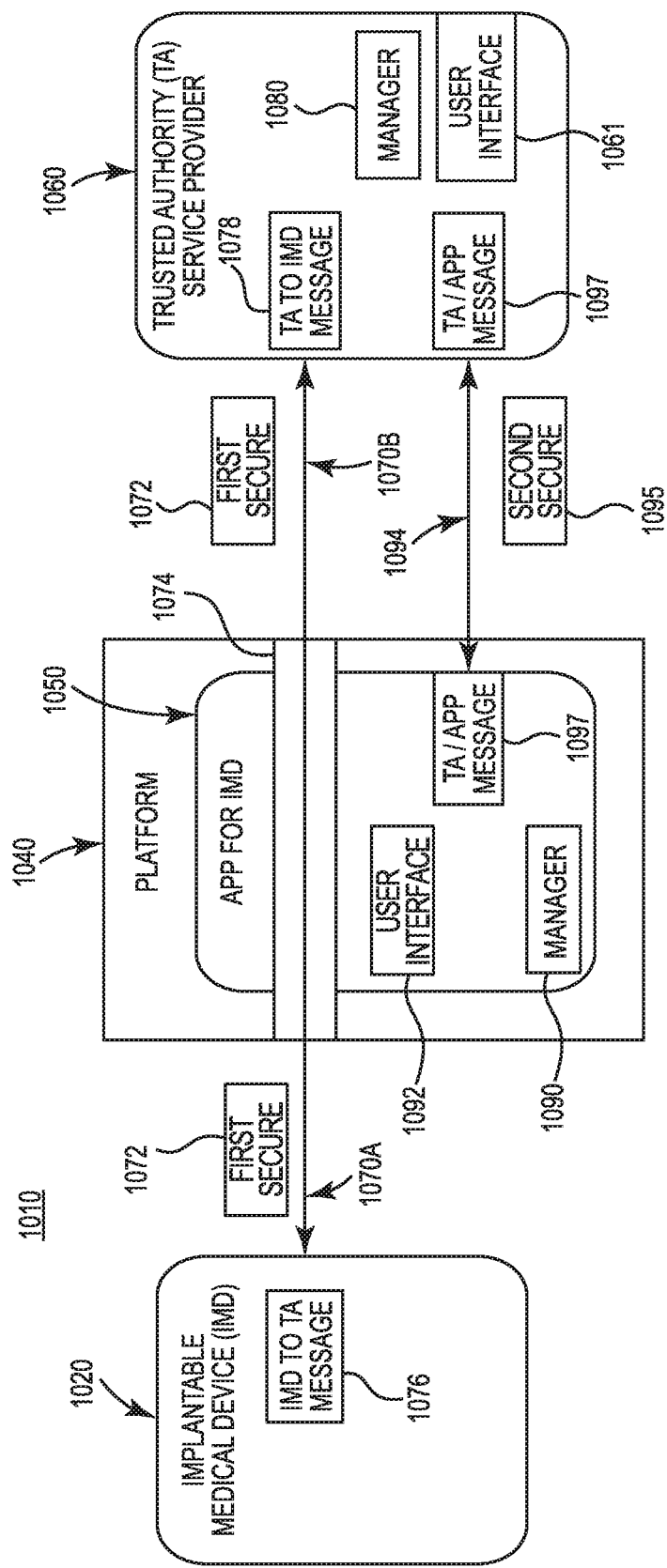
FIG. 3 is a block diagram schematically representing a system including a communication platform, according to one example of the present disclosure.

FIG. 3 is a block diagram of a system 1010, according to one example of the present disclosure. In some examples, system 1010 comprises at least some of substantially the same features and attributes of system 10 (FIG. 1A) and/or related examples (FIGS. 1B-2E). In some examples, system 1010 may comprise one implementation of system 10 (FIG. 1A) and/or the related examples (FIGS. 1B-2E). Accordingly, elements 1020, 1040, 1050, 1060 in FIG. 3A exhibit reference numerals like that of the analogous elements 20, 40, 50, 60 in FIG. 1A. As shown in FIG. 3, system 1010 includes an implantable medical device (IMD) 1020, a communication platform 1040 including an IMD application 1050, and a trusted authority (TA) service provider 1060. In some examples, the IMD application 1050 is executable via the communication platform 1040 and may or may not be hosted via a portion of the communication platform 1040.

In substantially the same manner as previously described for system 10 (at least FIG. 1A), the IMD application 1050, in association with communication platform 1040, acts as an intermediary for first secure communications 1070A, 1070B between the IMD 1020 and the TA service provider 1060. In some examples, the first security mechanism 1072 (e.g. security elements 1072) associated with the first secure communications 1070A, 1070B prevents access to the first secure communications 1070A, 1070B by the communication platform 1040 and by the IMD application 1050 while permitting secure access to the first communications 1070A, 10708 at the IMD 1020 and at the TA service provider 1060.

In some instances at least a portion of the communication platform 1040 may take the form of one of several different types of devices 142-175 as previously described in association with FIG. 1D.

Figure 4A:
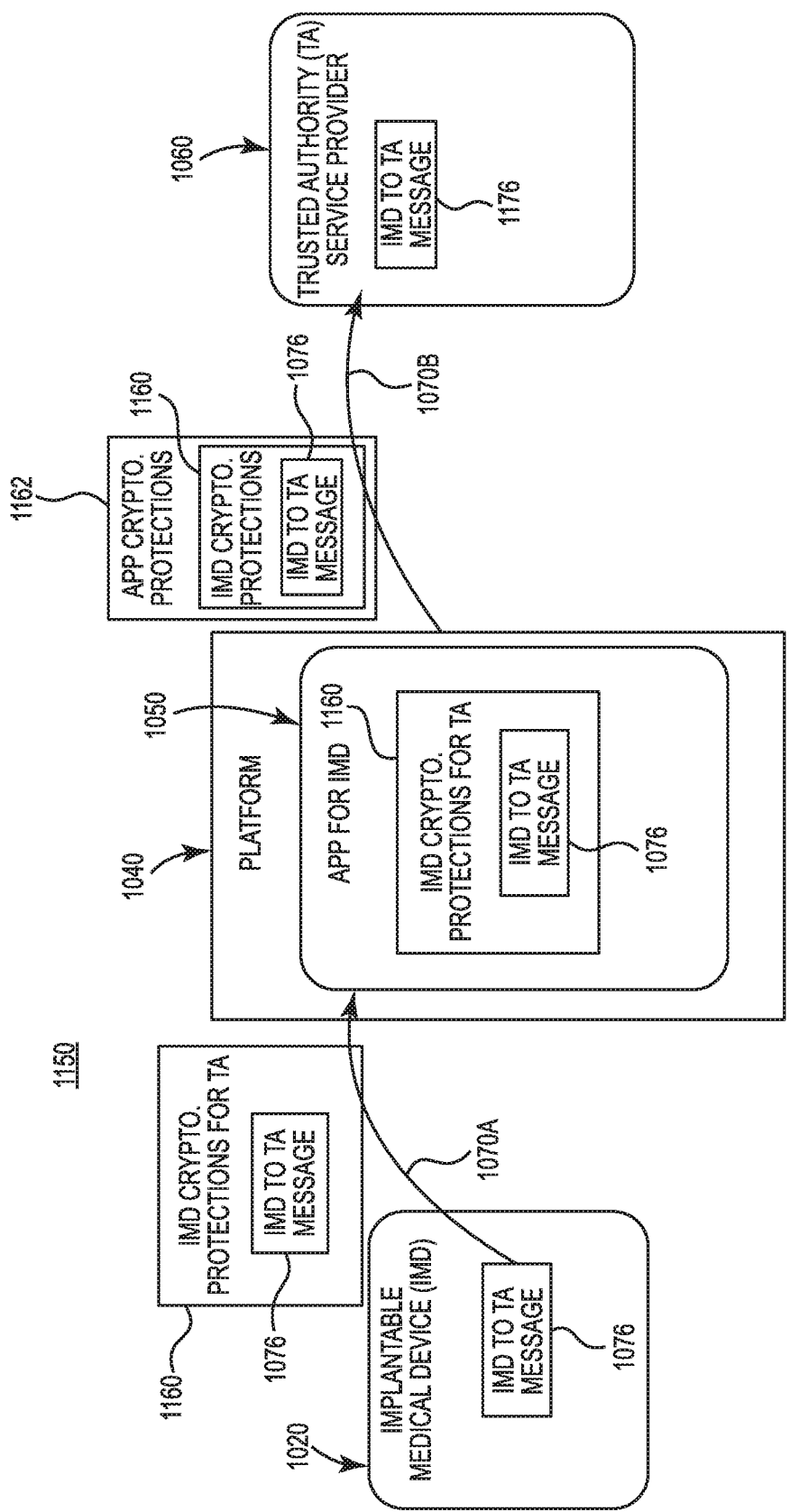
FIG. 4A is a block diagram schematically representing a system including a communication platform, according to one example of the present disclosure.

With this general arrangement of system 1010 in FIG. 3 in mind, it will be understood that FIGS. 4A-1I provide more specific examples of various implementations and details regarding the operation and interaction of at least IMD 1020, communication platform 1040, IMD application 1050 and/ or TA service provider 1060. With this in mind, it is noted that FIG. 8 provides just one example representation of comprehensive of the interactions among IMD 1020, communication platform 1040, IMD application 1050, and TA service provider 1060, as well as other elements.

In addition, in a manner similar to that described in association with at least FIG. 1H, in some examples at least system 1010 shown in FIG. 3 supports second secure communications 1094 (per second security element 1095) between IMD application 1050 and TA service provider 1060. With this in mind, one instance of second secure communications 1094 is further represented as TA/App message 1097 as shown in FIG. 3. Meanwhile, in some examples one instance of first communications 1070A is further represented as IMD to TA message 1076 while one instance of first communications 10708 is further represented as TA to IMD message 1078. It will be understood that the term "message" does not strictly refer to a messaging protocol, such as SMS, but may generally represent wired or wireless communication between two entities and which is performed in a secure format as described within at least some examples of the present disclosure.

In a manner similar to that previously described in association with at least FIG. 1C, in some examples, the IMD 1020 may comprise a communications security manager (e.g. 22 in FIG. 1C) to manage security mechanisms at the IMD 1020 and in some examples, the TA service provider 1060 may comprise a communications security manager (e.g. 62 in FIG. 1C) to manage security mechanisms at the TA service provider 1060.

In some examples, the security mechanisms associated with the respective first and second communications and implemented via at least the respective security managers (e.g. 22, 62 in FIG. 1C) include cryptographic technologies, at least some of which were previously described in association with at least FIGS. 1A-2E and which are further described below illustrated in association with at least FIGS. 4A-15.

In some examples, the IMD application 1050 includes a user interface 1092. In some instances, user interface 1092 includes an input mechanism and a display with user interface 1092 being implemented a corresponding graphical user interface of the mobile device 1040. In some examples, user interface 1092 embodies at least some of substantially the same features and attributes as user interface 1486 as described in association with at least FIG. 11. In some examples, user interface 1092 comprises at least some of substantially the same features as user interface 600 as previously described in association with at least FIG. 2E. In some examples, user interface 1092 comprises at least some of substantially the same features as performance manager 500 as previously described in association with at least FIG. 2D.

Accordingly, in some examples, upon implementing the performance engine 500 in the IMD application 1050, a performance manager 1090 is accessible and implementable via user interface 1092. In some examples, the manager 1090 is primarily accessible and/or used by the patient and as such may sometimes be referred to as a patient performance manager 1090. The patient performance manager 1090 enables a patient to monitor and/or control at least some operations of the IMD 1020, as permitted by the manufacturer of the IMD 1020 and/or the clinician responsible for the patient. For instance, a patient may be permitted via patient performance manager 1090 to make adjustments in the intensity of stimulation with such adjustments being within an absolute range set by the manufacturer and with a relative range (which is within the absolute range) set by the clinician. Other patient-controllable performance parameters may include an on/off function, programmed start/end times, delayed start, and the like which are within the ambit of decisions suitably made by a patient.

In some examples, the TA service provider 1060 includes a master performance manager 1080, which enables a clinician to monitor and/or control at least some operations of the IMD 1020, as permitted by the manufacturer of the IMD 1020. For instance, a clinician may be permitted via a master performance manager 1080 to make adjustments in various parameters regarding stimulation therapy. In one example, the master performance manager 1080 permits the clinician to set the relative range of values for each of certain parameters modifiable to the patient with such adjustments being within an absolute range of values set by the manufacturer and in compliance with medical regulatory frameworks. In some examples, such control by the clinician may be at least partially implemented via a rules function 1378 as further described in association with management engine 1350 in association with at least FIG. 6A.

Accordingly, patient performance manager 1090 and master performance manager 1080 implement parameters of the IMD 1020 within constraints set by the manufacturer of the IMD 1020, which also are within constraints determined and/or approved within a medical regulatory framework. It will be understood that the constraints on parameters, functions, and engines of IMD 1020 in each of the patient performance manager 1090 and master performance manager 1080 are appropriate to the respective roles (e.g. patient, clinician respectively) in patient care. In some examples, manager 1080 of TA service provider 1060 is at least partially implemented, displayable, and/or operable via a user interface 1061 of TA service provider, as shown in FIG. 3. In some examples, manager 1090 of IMD application 1050 is at least partially implemented, displayable, and/or operable via a user interface 1092 of IMD application 1050, as shown in FIG. 3.

With this in mind, FIG. 4A is a block diagram schematically illustrating an example implementation 1150 of the system 1010 in which the IMD application 1050 applies cryptographic security protections 1162 to the IMD-to-TA message 1076, which is already secured via cryptographic security protections 1160 originated by IMD 1020. Accordingly, this arrangement provides yet another example of the layered security approach (described in association with at least FIG. 1H) used when employing the IMD application 1050 (executable via communication platform 1040) to implement secure communications between the IMD 1020 and the TA service provider 1020.

Figure 5A:
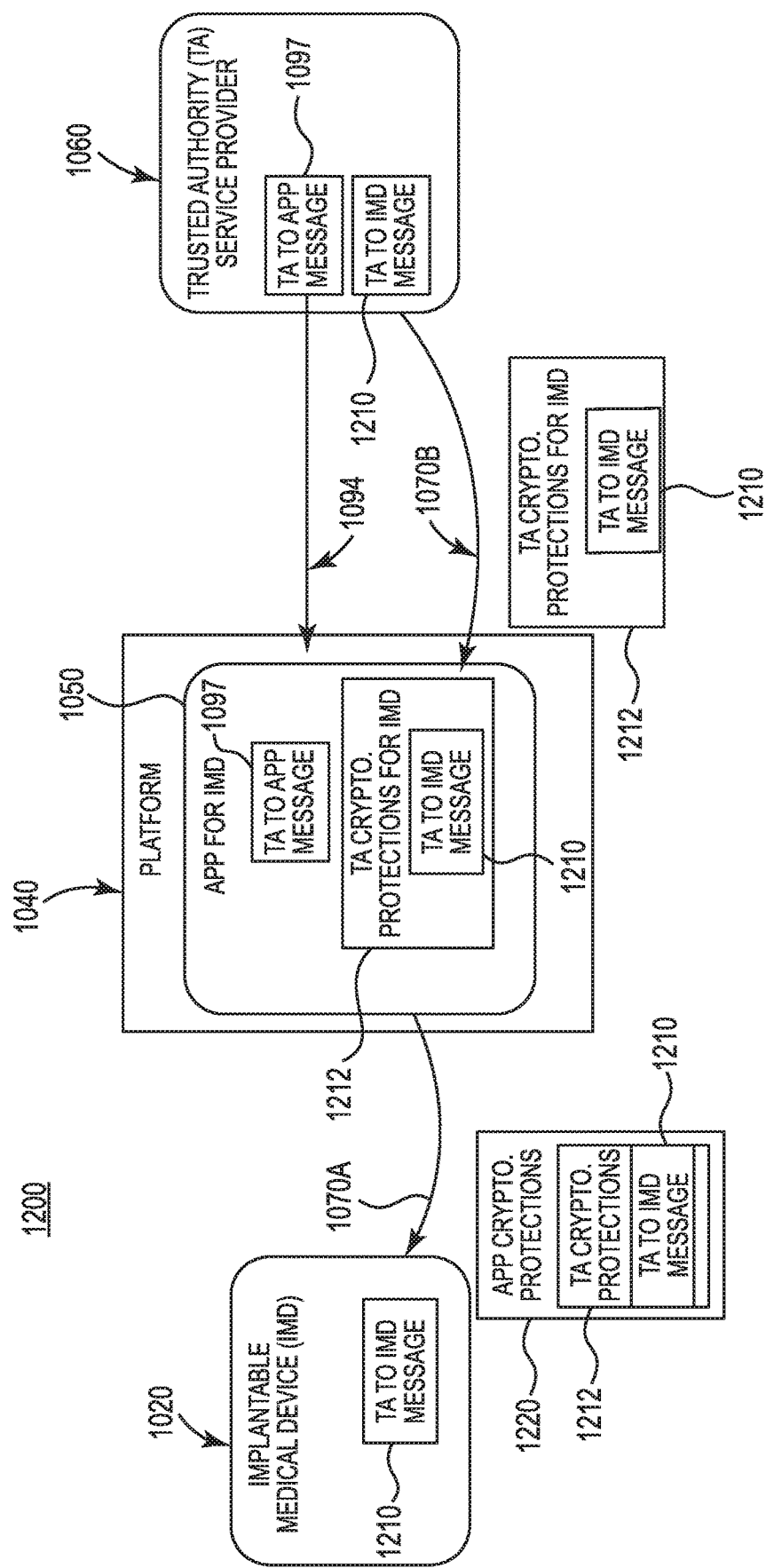
FIG. 5A is a block diagram schematically representing a system including a communication platform, according to one example of the present disclosure.

Similarly, FIG. 5A is a block diagram schematically illustrating an example implementation 1200 of the system 1010 in which the IMD application 1050 applies cryptographic security protections 1220 to the TA-to-IMD message 1210, which is already secured via cryptographic security protections 1212 originated by TA service provider 1060. Accordingly, this arrangement provides yet another example of the layered security approach used when employing the IMD application 1050 (executed via communication platform 1040) to implement secure communications between the IMD 1020 and the TA service provider 1060.

Figure 4B:
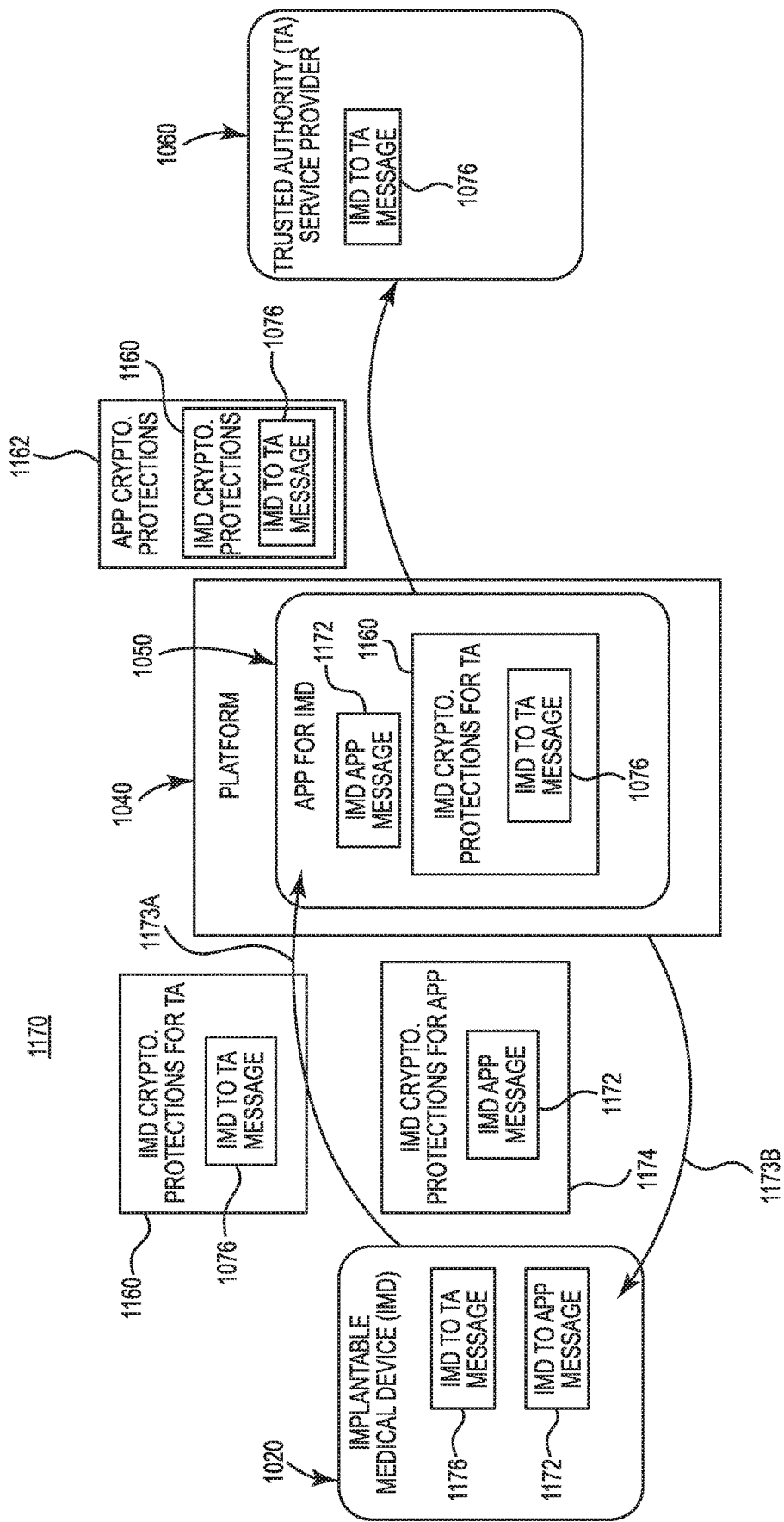
FIG. 4B is a block diagram schematically representing a system including a communication platform, according to one example of the present disclosure.

FIG. 4B is a block diagram schematically illustrating an example implementation 1170 of the system 1010 in which the IMD 1020 applies (as represented by directional arrow 1173A) cryptographic security protections 1174 to an IMD-to-application message 1172. In some examples, the application (e.g. App for IMD) 1050 may also apply similar cryptographic security protections 1174 to an application-to-IMD message, as represented by directional arrow 1173B. Via such an arrangement, in at least some instances, content may be directly communicated between the IMD 1020 and the IMD application 1050. At least one situation in which such direct communication of content may occur is when the TA service provider 1060 is unavailable to implement first or second secure communications or in situations for which the user should always have the ability (e.g. fail safe mode) to exert at least partial control over the IMD 1020, such as to turn the therapy off.

In some examples, the TA service provider 1060 may authorize the IMD application 1050 to communicate directly with the IMD 20 for a selectable, predetermined time period. The authorization may be renewable by the TA service provider in some examples. In some such examples, the authorization may include a unique IMD 1020, IMD application 1050 and communication platform 1040, user id, and/or wireless communication protocol id (e.g. Bluetooth ID).

In some examples, such authorization by the TA service provider 1060 may be implemented via an authority delegation function, such as but not limited to the authority delegation function 1376 of TA service provider 1060 as described in association with at least FIG. 6A.

In some examples, the TA service provider 1060 may provide authorization to the IMD application 1050 by communicating instructions (e.g. a recipe) for the IMD application 1050 to implement communications with IMD 1020, at least for a limited period of time.

In some examples, communication between IMD application 1050 and IMD 1020 such as via IMD-to-App message 1172 (and/or a corresponding App-to-IMD message) is authorized via a second authentication factor, which may be implemented via a second step authentication scheme, such as but not limited to authentication engine 350 as previously described in association with at least FIG. 11.

Figure 5B:
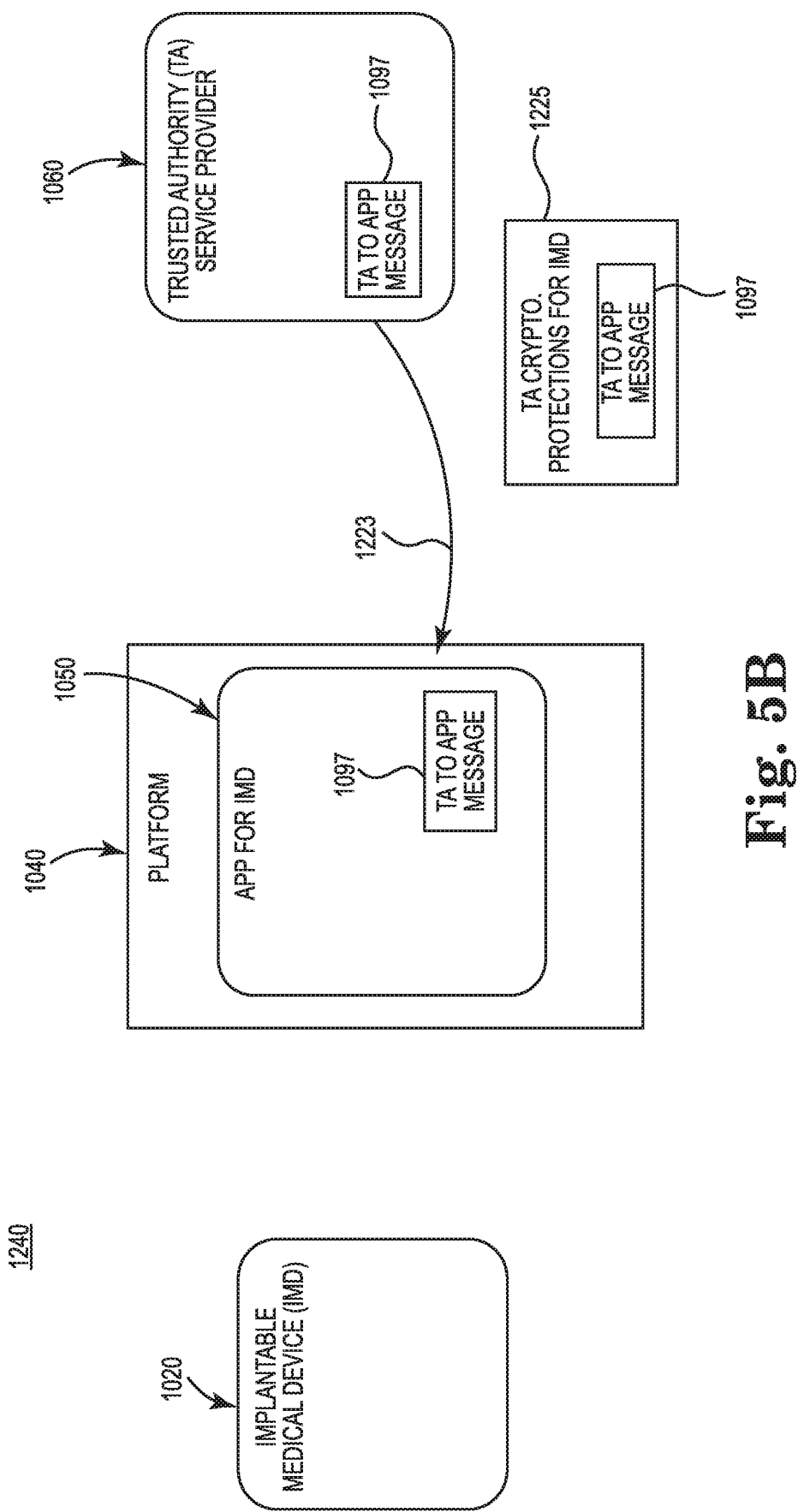
FIG. 5B is a block diagram schematically representing a system including a communication platform, according to one example of the present disclosure.

FIG. 5B is a block diagram schematically illustrating an example implementation 1240 of the system 1010 in which the TA service provider 1060 implements second secure communications 1223 via applying cryptographic security protections 1225 to an TA-to-application message 1097.

In some examples, message 1097 may include performance information to be displayed in a user interface (600 in FIG. 2E; 1092 in FIG. 3; and/or 1486 in FIG. 11) of the IMD application 1050.

With these more specific examples (FIGS. 3-5B) of secure communications in mind, further details regarding at least IMD application 1050, communications platform 1040 and/or TA service provider 1060 are provided below with such further details being applicable (in at least some instances) to the various examples of a IMD application (e.g. 50, etc.) and TA service provider (e.g. 60, etc.) throughout the present disclosure.

With this in mind, in some examples the TA service provider (e.g. 60 in FIG. 1A, 1060 in FIG. 3, etc.) comprises a management engine 1350 as shown in FIG. 6A, and which represents just some of the various functions implementable via the TA service provider 1060. In some examples, the management engine 1350 operates in cooperation with and/or is implemented via user interface 1061 and/or manager 1080 of TA service provider 1060 as shown in FIG. 3. Accordingly, from time-to-time at least some examples of the present disclosure may refer with particularity to the management engine 1350 of FIG. 6A, it will be understood that the features and functions specifically addressed in association with FIG. 6A do not limit the full range of features, functions, and/or modalities of TA service provider 1060 as disclosed throughout examples of the present disclosure.

In some examples, as shown in at least FIG. 6A, the management engine 1350 of the TA service provider 1060 includes a provisioning element 1370 or service for initiating communication with the IMD 1020 via an IMD application 1050 (associated with the communication platform 1040) and associating at least a portion (e.g. a communication device) of the communication platform 1040 (via the IMD application 1050) with at least the patient and the IMD 1020, and in some instances with a clinician. As further described later, the TA service provider 1060 (FIG. 3) develops and assigns cryptographic keys as appropriate. In some examples, while the IMD 1020 may have capabilities for provisioning, the TA service provider 1060 initiates provisioning between the TA service provider 1060 and the IMD 1020.

In some examples, as shown in at least FIG. 6A, the management engine 1350 of the TA service provider 1060 (FIG. 3) includes a verification service function 1372, such as a service for verifying that a system user and communication platform 1040 (executing IMD application 1050) have authority to communicate with and review data from a particular IMD 1020. In some examples, the TA service provider 1060 may further customize the controls and information accessible to the user (via IMD application 1050) based on the user type and configuration of the IMD 1020.

In some examples, the TA service provider 1060 (FIG. 3) includes a security manager (62 in FIG. 1C) to implement cryptographic technologies to secure communications with the IMD 1020 via an otherwise unsecured channel (such as via a non-IMD-dedicated communication platform 1040), as previously described in association with FIG. 1A. In some examples, the security manager 62 forms part of and/or cooperates with manager 1080 (FIG. 3)

In some examples, as shown in at least FIG. 6A, the management engine 1350 of the TA service provider 1060 (FIG. 3) includes a medical safeguard function 1374 to implement medical grade safeguards for communications with the IMD 1020 such that the safeguards associated with the use and control of the IMD 1020 (in association with IMD application 1050 on non-IMD-dedicated communication platform 1040) are substantially similar to those provided in an external device dedicated to controlling the IMD 1020, such as a medical grade external device provided by the manufacturer of the IMD 1020.

In some examples, the TA service provider 1060 includes a user interface 1061 (FIG. 3), which among other functions may allow users (e.g. clinicians) to modify IMD parameters. In some examples, this user interface comprises at least some of substantially the same features as user interface 600 (FIG. 2E), 1092 (FIG. 3, and/or 1486 (FIG. 11). In some examples, this user interface comprises at least some of substantially the same features as performance manager 500 (FIG. 2D).

In some examples, the TA service provider 1060 includes an user interface 1061 as shown in FIG. 3 to allow users to review and generate reports on IMD data as well as non-IMD data relevant to the medical condition, whether the data is collected by the IMD application 1050 (on the non-IMD-dedicated communication platform 1040) and/or peripherals attached to it. In some examples, some peripherals include sensors, as further described in association with at least FIGS. 2A-2C. In some examples, this user interface 1061 comprises at least some of substantially the same features as user interface 600 (FIG. 2E), 1092 (FIG. 3), and/or 1486 (FIG. 11). In some examples, at least some aspects of this user interface 1061 can be implemented via reporting function 634 of user interface 600 (FIG. 2E). In some examples, at least some aspects relating to reporting in association with user interface 1061 comprises at least some of substantially the same features as performance manager 500 (FIG. 2D).

In some examples, via its communication with IMD application 1050, the TA service provider 1060 (FIG. 3) provides a communication link between caregivers (at the TA service provider 1060) and patients (at the IMD application 1050 on communication platform 1040). This communication link aids in long term patient care, as well as providing immediate support when appropriate. In some examples, such a communication link may provide one example implementation of and/or comprises at least some of the substantially the same features as one of communication links previously described in association with communication engine 602 of user interface 600 in FIG. 2E.

In some examples, at least when implemented as a non-IMD-dedicated device (e.g. a consumer communication device), communication platform 1040 (FIG. 3) includes a communications system compatible with the IMD 1020. In some examples, the non-IMD-dedicated communication platform 1040 incorporates hardware support and/or software support for additional relevant sensor and communication tools (e.g. Bluetooth for pulse oximetry, serial for other sensors, audio for communications, etc.)

In some examples, the communication platform 1040 (FIG. 3) incorporates tools to verify that the communication platform 1040 and IMD application 1050 are compatible and usable as well as to verify that the communication platform 1040 and IMD application 1050 have not been tampered with. In some examples, this verification may be at least partially implemented in association with verification function 640 accessible via user interface 600 (FIG. 2E).

In some examples, the IMD application 1050 (FIG. 3) executed via the communication platform 1040 (e.g. consumer communication device in some examples) has the ability to add its signature and temporal parameters to messages between IMD 1020 and TA service provider 1060 to allow verification of the communication channel therebetween. In some examples, such verification may be embodied as part of communication engine 602 of user interface 600 (FIG. 2E) generally and in particular, in association with elements 604, 606 and/or 608 of communication engine 602. In some examples, whether in cooperation with communication engine 602 or independently, such verifications may be at least partially implemented via verification function 640 in user interface 600 as previously described in association with at least FIG. 2E.

In some examples, the IMD application 1050 (FIG. 3) does not have an ability to read or modify secured communications between IMD 1020 and TA service provider 1060, despite such communications passing through the communication platform 1040 executing the IMD application 1050. Stated differently and as previously noted, the first secure communications prevent such access.

In some examples, the IMD application 1050 (FIG. 3) provides an user interface (e.g., 600 in FIG. 2E, 1092 in FIG. 3; and/or 1486 in FIG. 11) appropriate to user privileges to review data from the trusted authority (TA) service provider 1060 as well as request performance changes regarding the IMD 1020, such as (but not limited to) via the various functions of user interface 600 (FIG. 2E) and/or performance engine 500 (FIG. 2D).

In some examples, the IMD application 1050 (FIG. 3) collects data from sensors (at least FIGS. 2A-2C) relevant to the medical condition, cryptographically protects data (integrity, confidentiality, and temporal nature) and provides data to trusted authority (TA) service provider 1060. Of course, the second secure communications described throughout examples of the present disclosure provide one pathway to at least partially implement such functionality of the IMD application 1050.

In some examples, at least via second secure communications 1094 (FIG. 3) between the IMD application 1050 and the TA service provider 1060, the IMD application 1050 provides the ability for mutual communication between patients (at IMD application 1050) and clinicians (at TA service provider 1060).

In some examples, the IMD application 1050 (FIG. 3) verifies that the communication platform 1040 has appropriate hardware and software platform capability to safety and effective utilize the IMD application 1050 and interact/communicate with the TA service provider 1060 and the IMD 1020.

In some examples, the IMD application 1050 (FIG. 3) may allow for certain safety sensitive commands (such as dictated according to a medical regulatory framework) to be sent to the IMD 1020 without the involvement or presence of the TA service provider 1060.

In some examples, depending on a relative safety profile of the therapy, the TA service provider 1060 (FIG. 3) may delegate authority to the IMD application 1050 to control certain types of commands. Accordingly, in some examples, as shown in at least FIG. 6A, the management engine 1350 comprises an authority delegation function 1376. In some instances, the delegation may be permanent and in some instances, the delegation may be for limited periods of time. In some instances, the TA service provider 1060 may delegate limited authority to an emergency technician (EMT) to all access devices via a "safe mode", which can enable the EMT to treat a patient (having an IMD 20) via an IMD application 1050 or via another device available to the EMT which can mimic control by the IMD application 1050/non-IMD communication platform 1040.

In some instances, via the authority delegation function 1376 (FIG. 6A), the TA service provider 1060 may delegate authority for more detailed access by clinicians to a large number of devices (IMD 1020 and/or corresponding IMD application 1050 (as executed via communication platform 1040)) to enable the clinicians to track and/or treat their patients. In some instances, the clinician level of authority/access may be employed for research purposes in which the clinician can track trends and patterns in therapy efficacy.

In some instances, via the authority delegation function 1376 (FIG. 6A), the TA service provider 1060 may delegate authority to a patient or caregiver for limited access for minimal therapy changes/operation to just one IMD 1020 via an associated IMD application 1050 (executable via communication platform 1040).

In some examples, at least one implementation of the authority delegation function 1376 (FIG. 6A) of management engine 1350 of TA service provider 1060 is previously described in association with at least FIG. 4B.

With further reference to FIG. 3, in some examples, the IMD application 1050 (as executed via communication platform 1040) implements asymmetric keys as a security mechanism to sign/protect communications (e.g. messages) that would only be able to be read by the TA service provider 1060.

In some examples, the IMD application 1050 (as executed via communication platform 1040) does not have access to symmetric keys of the IMD 1020 and TA service provider 1060 because such access might otherwise subject such communications between the IMD 1020 and the TA service provider 1060 to attack. In some examples, such symmetric keys used in communications between the IMD 1020 and the TA service provider 1060 prevent access by the IMD application 1050.

In some examples, the TA service provider 1060 (FIG. 3) can assign a new public key to the IMD application 1050 when the IMD application 1050 is authorized by the TA service provider 1060.

In some examples, a private key may be shared with the IMD 1020 along with temporal parameters and other hardware parameters (e.g. Bluetooth address, IP address, MAC address, version of the IMD application 1050 (as executed via communication platform 1040) so the private key can directly identify the communication platform (e.g. consumer communication device, in some examples).

In some examples, de-authorization of the IMD application 1050 (as executed via communication platform 1040) can occur upon natural expiration of a public key due to temporal parameters or forced de-authorization facilitated by the TA service provider 1060.

In some examples, in coordination with at least communication platform 1040 on which it is executed, the IMD application 1050 can include methods and/or elements to allow the IMD application 1050 to self-verify normal operation, such as evaluating its memory space against values that were compiled in or provided by the TA service provider 1060. This arrangement may provide an additional layer of protection against reverse engineering or other unwanted manipulation.

In some examples, all communications between the communication platform 1040 (including application 1050) and the TA service provider 1060 can be further encrypted utilizing security protocols to maintain communication confidentiality, integrity, and availability. In one such example, the communications are performed via a Secure Socket Layer (SSL) protocol. In one aspect, this arrangement provides a redundancy to communications to provide additional protection.

In some examples, the IMD application 1050 includes at least one mechanism to verify normal operation of at least one of the IMD application 1050 and of the communication platform 1040 on which the IMD application 1050 is executable.

In some examples, in this context the term "normal operation" refers to uncorrupted operation of the IMD application 1050 and/or communication platform 1040, e.g. operation which has not been corrupted, compromised, hacked by unauthorized agents, such as but not limited to, an intrusion, alteration, etc. of IMD 1020, TA service provider 1060, communication platform 1040, IMD application 1050, and/or even a sensor (FIGS. 2A-2C).

In some examples, verifying normal operation of the IMD application 1050 (as executable on communication platform 1040) includes verifying that the user can see the pertinent information regarding operation of the IMD 1020, such as via a user interface (1092 FIG. 3; 600 in FIG. 2E; and/or 1486 in FIG. 11). In some examples, verifying normal operation of the IMD application 1050 (as executable via communication platform 1040) includes verifying support of the operating system of the communication platform 1040 and that the operating system is functioning normally. In other words, in some examples the IMD application 1050 verifies that the communication platform 1040 has not been jailbroken (e.g. Apple iOS), not been rooted (e.g. Android) or otherwise unlocked in a manner to bypass the manufacturer's intended environment/constraints of the operating system of the communication platform 1040.

In some examples, verifying normal operation of the IMD application 1050 (as executable on the communication platform 1040) includes verifying that the IMD application 1050 has not been tampered with, such as via tamper resistance tools. In some examples, tamper resistance tools include self-hashing techniques and/or self-evaluation of execution metrics and pathways. In some instances, this self-verification includes the IMD application 1050 (as executable via the communication platform) using redundant steps to verify its output. In some examples, such verification may be at least partially implemented via at least verification function 640 (FIG. 2E) and/or communication engine 602 (FIG. 2E).

In some examples, more than one of the identified self-verification techniques is implemented in association with the IMD application 50.

In view of these various examples of the IMD 1020, IMD application 1050, TA service provider 1060 (and others described in the present disclosure), it will be understood that in some examples the TA service provider 1060 may manage multiple IMDs 1020 (and associated IMD applications 1050) in which the multiple IMDs 1020 belong to a single patient or in which the multiple IMDs 1020 (and associated IMD applications 1050) are dispersed among different patients.

Moreover, it will be further understood that in some examples, via their respective managers 1090, 1080, the TA service provider 1060 and/or IMD application 1050 may manage multiple types of IMDs 1020. For instance, some types of IMD 1020 may be adapted to treat obstructive sleep apnea, while other types of IMDs 1020 may be adapted to treat cardiac irregularities or may be adapted to treat urinary incontinence, for pain management, diabetes, other types of neurostimulation, etc. In addition, while some types of IMD 1020 managed by TA service provider 1060 and/or IMD application 1050 may involve neurostimulation, other types of IMDs 1020 managed by TA service provider 1060 and/or IMD application 1050 may involve other types of non-neurostimulation therapies such as, but not limited to, fluid delivery (e.g. pharmaceutical and/or non-pharmaceutical).

With continued reference to FIG. 3, in some examples via a manager (e.g. manager 1080 in FIG. 3), the TA service provider 1060 may store performance information for patients with IMDs 1020, which may then be accessed by a clinician or hospital to treat a particular patient on acute basis and/or to study and learn how to better manage the patient's therapy over time and/or to better utilize IMD 1020. In some examples, via its manager 1080 (FIG. 3), the TA service provider 1060 may collate such data for many patients having IMDs 1020 (such as those managed via an IMD application 1050) to provide a data repository from which data can be mined for indicators or disease progression or emergence of related disease states.

Figure 6B:
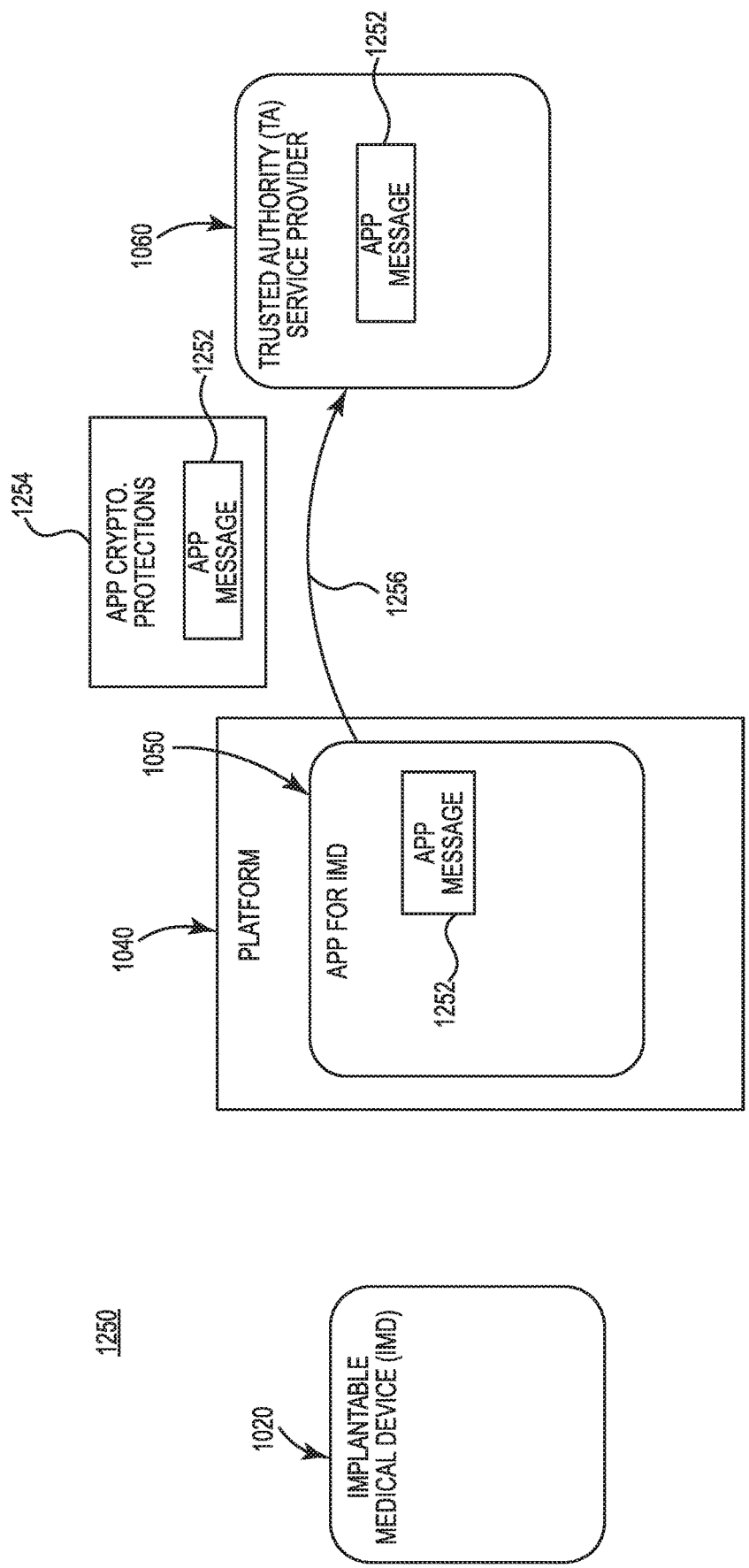
FIG. 6B is a block diagram schematically representing a system including a communication platform, according to one example of the present disclosure.

In some examples, as shown in FIG. 6B, the IMD application 1050 transmits a message 1252 as part of second secure communications 1256 to the TA service provider 1060, wherein the second secure communications 1256 include patient input regarding therapy and/or relevant medical, situational, and qualitative information. In some examples, second secure communications 1256 are implemented via security mechanism 1254, such as cryptographic protections applied by the IMD application 1050. In some examples, message 1252 may correspond to and/or include a sensor message 1312 as later described in association with at least FIG. 7.

FIG. 7 is a block diagram 1300 schematically representing a system in which the IMD application 1050 receives sensed information from a sensor 1310 regarding a physiologic state of the patient. In some examples, sensor 1310 comprises at least some of substantially the same features and attributes as at least one of the sensors previously described in association with at least FIG. 2A, 2B, or 2C.

In some examples, the IMD application 1050 displays the sensed information in association with the communication platform 1040, such as via user interface 1092 (FIG. 3; and/or 600 in FIG. 2E; 1486 in FIG. 11) of the IMD application 1050. In some examples, the IMD application 1050 displays the sensed information in association with at least sensing function 534 of the performance engine 500 in FIG. 2D. In some examples, the IMD application 1050 displays the sensed information in association with at least sensing function 632 and/or reporting function 634 of the user interface 600 in FIG. 2E.

In some examples, the IMD application 1050 communicates the sensed information via a sensor message 1312 (FIG. 7) as part of second secure communications 1322 (including security mechanism 1320) from the IMD application 1050 to the trusted authority (TA) service provider 1060.

In some examples, via its manager 1080 (FIG. 3), the trusted authority (TA) service provider 1060 includes a performance manager (e.g. performance engine 500 in FIG. 2D) to evaluate, based at least partially on the sensed information, the performance associated with the IMD 1020.

In addition, as further shown in FIG. 5B, in some instances the TA service provider 1060 transmits second secure communications 1223 (including TA to App message 1097) to the IMD application 1050 regarding such IMD performance.

In some examples, a performance manager 1080 (FIG. 3) of the trusted authority (TA) service provider 1060 includes an auto-titration manager to selectively implement an adjustment, at the IMD 1020 via first secure communications (e.g. 1070A, 1070B in FIG. 3) from the trusted authority (TA) service provider 1060, through the communication platform 1040, to the IMD 1020. In some examples, the adjustment is at least partially based on sensed physiologic-related information. In some examples, performance manager 1080 comprises at least some of substantially the same features and attributes as performance engine 500 in FIG. 2D. In some examples, performance manager 1080 provides one example implementation of at least some aspects of performance engine 500 (FIG. 2D).

In some examples, the auto-titration manager may be at least partially implemented via a rules function 1378 of management engine 1350 as shown in FIG. 6A, and by which the degree and type of adjustments are configurable according to rules set by a clinician and which may be based according to performance of the implantable medical device. The clinician sets a patient's selectable range for intensity of stimulation (e.g. a maximum and a minimum), a magnitude of change for each incremental input available to the patient, ranges for time periods of use, etc. The clinician may also set parameters to enable an automatic change to the patient's intensity of stimulation in response to changes in the performance of the implantable medical device. It will be understood that the rules are not limited solely to an intensity of stimulation but may include a full range of parameters relating to the performance of the implantable medical device 1020.

As previously mentioned, FIG. 8 provides one example of some comprehensive secure interactions and communications among an IMD, a communications platform including an IMD application, and a TA service provider as consistent with at least some examples previously described in association with at least FIGS. 1-7 and/or to be described later in association with FIGS. 9-15. It will be understood that operation of the example system or arrangements in FIG. 8 do not require each and every communication and interaction shown, but rather any combination of various interactions and communications may take place selectively.

FIG. 9 is a block diagram 1400 schematically representing a system 1401, according to one example of the present disclosure. As shown in FIG. 9, system 1401 includes IMD 1020, a trusted authority (TA) service provider 1060, a first secure communication path 1405A, 1405B between the IMD 1020 and the trusted authority (TA) service provider 1060. In some examples, the first secure communication path 1405A, 1405B includes a secure communication device 1410 operably couplable relative to the IMD 1020 to transmit therapy information from the IMD 1020 to the trusted authority (TA) service provider 1060 and to transmit therapy parameters from the trusted authority (TA) service provider 1060 to the IMD 1020.

As further shown in FIG. 9, the system 1401 includes an IMD application 1050 (executable via communication platform 1040) and establishes a second secure communication path 1415 between the IMD application 1050 and the trusted authority (TA) service provider 1060. In one aspect, the IMD application 1050 receives user input via a user interface 1092 (and/or 600 in FIG. 2E; 1486 in FIG. 11) of the IMD application (as executable via communication platform 1040) and can transmit the user input to the trusted authority (TA) service provider 1060 via the second secure communication path 1415 to at least partially manage operations of the IMD 1020 and/or communicate in order to receive information from the IMD 1020.

In some examples, the second secure communication path 1415 is separate from, and independent of, the first secure communication path 1405A, 1405B. In some examples, the second secure communication path 1415 is implemented via the examples of secure communications and/or security mechanisms between IMD application 1050 and TA service provider 1060 as previously described in association with at least FIGS. 1A-8.

In some examples, the first secure communication path 1405A, 1405B is provided via secure communication device 1410 including a telemetry tool to securely receive information directly from the IMD 1020 and a tool (e.g. telephony or other means) to securely send the received information to the trusted authority (TA) service provider 1060. In some examples, the secure communication device 1410 can securely receive information from the trusted authority (TA) service provider 1060 (whether via telephony or other means) and the IMD 1020 can securely receive information from the secure communication device 1410 via telemetry.

In some examples, the IMD application 1050 receives performance information from the trusted authority (TA) service provider 1060 and displays the received performance information via the user interface 1092 (at least 600 in FIG. 2E, 1486 in FIG. 11). In some examples, the IMD application 1050 sends performance requests/input (which may include patient therapy requests, in some example) to TA service provider 1060 and displays related performance information.

In some examples, the IMD 1020, IMD application 1050 (executable via communication platform 1040), and/or TA service provider 1060 in system 1401 include at least some of substantially the same features and attributes as described throughout the present disclosure in association with FIGS. 1A-8, 10-15, at least to the extent that such features and attributes are consistent with and/or complement the components, devices, etc. of system 1401.

In some examples, the first secure communication path 1405A, 1405B and/or secure communication device 1410 is implementable via existent remote monitoring systems, such as but not limited to, the type of remote patient monitoring systems available under the trade name Carelink™ from Medtronic, Inc. As such, in some examples, the secure communication device 1410 may comprise an "off-the-shelf" medical controller/monitor already available for use and communication with a particular IMD 1020 or adapted for use with other IMDs 1020. It will be understood that in some examples, an existent secure communication device 1410 may be adapted for use with IMD 1050 via programming changes via TA service provider 1060 or via hardware updates, which adapt the existent secure communication device 1410 for use with the IMD 1020, IMD application 1050, and TA service provider 1060 in a manner consistent with at least some examples of the present disclosure.

FIG. 10 is a block diagram 1481 schematically representing a control portion 1480, according to one example of the present disclosure. In some examples, control portion 1480 includes a controller 1482 and a memory 1484. In some examples, control portion 1480 provides one example implementation of a control portion forming a part of any one of IMD (20, 220, 1020, etc.), communication platform (40, 240, 1040 etc.), and/or trusted authority (TA) service provider (60, 260, 1060, etc.) as represented throughout the present disclosure in association with at least FIGS. 1A-9. In some examples, one example control portion 1480 implements IMD application 1050 on or via communication platform 1040.

In general terms, controller 1482 of control portion 1480 comprises at least one processor 1483 and associated memories. The controller 1482 is electrically couplable to, and in communication with, memory 1484 to generate control signals to direct operation of at least some components of the systems, components, engines, functions, tools, parameters, managers, mechanisms, applications, interfaces, and/or elements described throughout the present disclosure. In some examples, these generated control signals include, but are not limited to, employing manager 1485 stored in memory 1484 to manage performance of the IMD 1020 (including but not limited to patient therapy) and/or manage security of communications/operation of the IMD 1020, IMD application 1050 (as executable via communication platform 1040), and/or trusted authority (TA) service provider 1060 in the manner described in at least some examples of the present disclosure. It will be further understood that control portion 1480 (or another control portion) may also be employed to operate general functions of the IMD 1020, communication platform 1040, IMD application 1050, and/or trusted authority service provider 1060.

In response to or based upon commands received via a user interface (e.g. 600 in FIG. 2E; 1092 in FIG. 3; and/or 1486 in FIG. 11) and/or via machine readable instructions, controller 1482 generates control signals to implement performance monitoring/management (including therapy in some examples) and/or security in communications/operations in accordance with at least some of the previously described examples of the present disclosure. In some examples, controller 1482 is embodied in a general purpose computing device while in other examples, controller 1482 is embodied in the IMD 1020, communication platform 1040, IMD application 1050, and/or trusted authority (TA) service provider 1060 generally or incorporated into or associated with at least some of the associated components described throughout the present disclosure.

For purposes of this application, in reference to the controller 1482, the term "processor" shall mean a presently developed or future developed processor (or processing resources) that executes sequences of machine readable instructions contained in a memory. In some examples, execution of the sequences of machine readable instructions, such as those provided via memory 1484 of control portion 1480 cause the processor to perform actions, such as operating controller 1482 to implement performance management/monitoring (including therapy in some examples) and/or security in communications/operations, as generally described in (or consistent with) at least some examples of the present disclosure. The machine readable instructions may be loaded in a random access memory (RAM) for execution by the processor from their stored location in a read only memory (ROM), a mass storage device, or some other persistent storage (e.g., non-transitory tangible medium or non-volatile tangible medium, as represented by memory 1484. In some examples, memory 1484 comprises a computer readable tangible medium providing non-volatile storage of the machine readable instructions executable by a process of controller 1482. In other examples, hard wired circuitry may be used in place of or in combination with machine readable instructions to implement the functions described. For example, controller 1482 may be embodied as part of at least one application-specific integrated circuit (ASIC). In at least some examples, the controller 1482 is not limited to any specific combination of hardware circuitry and machine readable instructions, nor limited to any particular source for the machine readable instructions executed by the controller 1482.

In some examples, user interface 1486 comprises a user interface or other display that provides for the simultaneous display, activation, and/or operation of at least some of the various components, systems, components, engines, functions, tools, parameters, managers, mechanisms, applications, interfaces, elements, features, and attributes of control portion 1480 and/or the various aspects of an IMD application 1050 (as executable via communication platform 1040) and/or trusted authority (TA) service provider 1060. In some examples, at least some portions or aspects of the user interface 1486 are provided via a graphical user interface (GUI). In some examples, as shown in FIG. 11, user interface 1486 includes display 1488 and input 1489. In some examples, user interface 1486 is implemented as or incorporates at least some aspects of user interface 600 in FIG. 2E and/or user interface 1092 in FIG. 3. In some examples, such user interfaces also may incorporate at least some aspects of performance engine 500 in FIG. 2D.

FIG. 12 is a flow diagram schematically representing a method 1700 of at least partially implementing secure communications, according to one example of the present disclosure. In some examples, method 1700 can be performed via at least some of the systems, components, engines, elements, parameters, managers, mechanisms, applications, interfaces, functions, tools, etc. as previously described in association with at least FIGS. 1-11. For instance, in one example implementation, the implementation associated with method 1700 can be embodied as machine readable instructions storable in a non-transitory computer readable storage medium and executable via a controller of a control portion, such as the arrangement described in association with at least FIG. 10. In some examples, method 1700 can be performed via at least some systems, components, engines, elements, parameters, managers, mechanisms, applications, interfaces, functions, tools, etc. other than previously described in association with at least FIGS. 1-11.

As shown in FIG. 12, at 1702 method 1700 comprises implementing, via a communication platform, first secure communications between an implantable medical device (IMD) and a trusted authority (TA) service provider. As further shown in FIG. 12, the first secure communications prevent access to the first secure communications by the communication platform (1704) while permitting access to the first secure communications at the implantable medical device and/or at the trusted authority (TA) service provider.

In some examples, the communication platform comprises a wireless communication element to implement the first secure communications at least partially wirelessly.

As shown via 1720 in FIG. 13, in some examples a method includes an example implementation 1720 further comprising implementing the first secure communications such that the communication platform does not receive instructions from the TA service provider regarding operations and/or performance of the implantable medical device (IMD). In some examples in which the communication platform comprises a controller, the example implementation comprises operating the controller and/or the implantable medical device without operational instruction from the trusted authority (TA) service provider.

However, it will be understood that in at least some such examples, the trusted authority (TA) service provider may still operate in a complementary or cooperative manner relative to implantable medical device (IMD) to at least partially implement security aspects of the first secure communications. Moreover, in such arrangements, in some examples the TA service provider may receive information from the implantable medical device (IMD) even though the implantable medical device (IMD) and/or communications platform do not receive operational and/or performance instruction from the TA service provider.

In some examples, method 1720 can be performed via at least some of the methods, systems, components, engines, elements, parameters, managers, mechanisms, applications, interfaces, functions, tools, etc. as previously described in association with at least FIGS. 1-12. For instance, in one example implementation, the arrangement shown at 1720 can be at least partially embodied as machine readable instructions storable in a non-transitory computer readable storage medium and executable via a controller of a control portion, such as the arrangement described in association with at least FIG. 10. In some examples, the arrangement shown at 1720 can be performed via at least some methods, systems, components, engines, elements, parameters, managers, mechanisms, applications, interfaces, functions, tools, etc. other than previously described in association with at least FIGS. 1-12.

As shown at 1730 in FIG. 14, in some examples a method including the example implementation 1730 further comprises an arrangement to implement the first secure communications to provide solely data to the trusted authority (TA) service provider. In this arrangement, the communication platform relays the data to the TA service provider but otherwise does not take other action. In this way, at least some aspects of the communication platform may be viewed as a data relay station which can receive data broadcast by the implantable medical device (IMD) and which makes such data available for reception by the trusted authority (TA) service provider. In some examples, such data comprises sensed information regarding a physiologic-related information regarding the patient and/or such data comprises performance information regarding the implantable medical device (IMD).

In some examples, the arrangement in 1730 can be performed via at least some of the methods, systems, components, engines, elements, parameters, managers, mechanisms, applications, interfaces, functions, tools, etc. as previously described in association with at least FIGS. 1-12. For instance, in one example implementation, the arrangement in 1730 can be at least partially embodied as machine readable instructions storable in a non-transitory computer readable storage medium and executable via a controller of a control portion, such as the arrangement described in association with at least FIG. 10. In some examples, the arrangement in 1730 can be performed via at least some methods, systems, components, engines, elements, parameters, managers, mechanisms, applications, interfaces, functions, tools, etc. other than previously described in association with at least FIGS. 1-12.

FIG. 15 is a diagram schematically representing a method 1800 of at least partially implementing secure communications, according to one example of the present disclosure. In some examples, method 1800 can be performed via at least some of the methods, systems, components, engines, elements, parameters, managers, mechanisms, applications, interfaces, functions, tools, etc. as previously described in association with at least FIGS. 1-12. For instance, in one example implementation, the implementation associated with method 1800 can be embodied as machine readable instructions storable in a non-transitory computer readable storage medium and executable via a controller of a control portion, such as the arrangement described in association with at least FIG. 10. In some examples, method 1800 can be performed via at least some methods, systems, components, engines, elements, parameters, managers, mechanisms, applications, interfaces, functions, tools, etc. other than previously described in association with at least FIGS. 1-12.

As shown at 1802 in FIG. 15, a method can at least partially implement second secure communications between the communication platform and the trusted authority service provider, wherein the second secure communications are separate from, and independent of, the first secure communications. In some examples, an application executable via (and/or associated with) the communication platform acts to send and/or receive the second secure communications relative to the trusted authority (TA) service provider. Via the application and the complementary relationship of the trusted authority (TA) service provider, a user of the communications platform such as a patient may at least partially monitor and/or at least partially control performance of an implantable medical device within their body.

Although specific examples have been illustrated and described herein, it will be appreciated by those of ordinary skill in the art that a variety of alternate and/or equivalent implementations may be substituted for the specific examples shown and described without departing from the scope of the present disclosure. This application is intended to cover any adaptations or variations of the specific examples discussed herein.

The invention claimed is:

1. A trusted authority service provider comprising:
a communication element;
an authority delegation function programmed to a controller;
a master performance manager programmed to the controller; and
the controller to:
implement, via the communication element, first secure communications relative to an implantable medical device through a non-IMD-dedicated communication platform, wherein the first secure communications prevent access to the first secure communications by the non-IMD-dedicated communication platform and permit secure access to the first secure communications at the implantable medical device and the trusted authority service provider,
implement, via the communication element, second secure communications relative to an IMD application associated with the communication platform,
implement, via the authority delegation function, authorizing the communication platform to communicate directly with the implantable medical device, and
form, via the mater performance manager, at least a portion of a first one of the first secure communications to change a performance of the implantable medical device in response to a first one of the second secure communications received from the IMD application requesting a change in performance of the medical device.

2. The trusted authority service provider of claim 1, wherein the implantable medical device comprises an active implantable medical device.

3. The trusted authority service provider of claim 1, the controller to at least partially manage operations of the implantable medical device (IMD) via the first secure communications.

4. The trusted authority service provider of claim 1, comprising:
a security manager to implement, as a trusted authority, a first security mechanism to encrypt the first secure communications from the trusted authority service provider to the implantable medical device and to implement a second security mechanism to decrypt first secure communications from the implantable medical device to the trusted authority service provider.

5. The trusted authority service provider of claim 4, the security manager to implement a third security mechanism to encrypt second secure communications from the trusted authority service provider to an IMD application associated with the communication platform and to implement a fourth security mechanism to decrypt second secure communications from the IMD application to the trusted authority service provider.

6. The trusted authority service provider of claim 5, wherein the second secure communications are separate from, and independent of, the first secure communications.

7. The trusted authority service provider of claim 6, wherein the communication platform comprises a first portion on which the IMD application is executable, wherein the first portion includes a first channel to implement the first secure communications and a second channel to implement the second secure communications, wherein the second channel is separate from, and independent of, the first channel.

8. The trusted authority service provider of claim 5, the trusted authority service provider to at least partially monitor operations of the implantable medical device via the first and second secure communications.

9. The trusted authority service provider of claim 5, wherein the second secure communications comprise at least partially the same data as the first secure communications between the implantable medical device and the trusted authority service provider.

10. The trusted authority service provider of claim 1, the controller to receive, via the first secure communications, sensed physiologic-related information regarding the patient.

11. The trusted authority service provider of claim 1, wherein the trusted authority service provider includes a performance manager to evaluate performance by the implantable medical device.

12. The trusted authority service provider of claim 11, wherein the performance evaluation is based at least partially on sensed physiologic-related information received from the implantable medical device via the first secure communications.

13. The trusted authority service provider of claim 11, the trusted authority (TA) service provider to transmit second secure communications to the IMD application, wherein the second secure communications include performance information displayable in a user interface of the IMD application.

14. The trusted authority service provider of claim 11, wherein the performance manager comprises a transfer function to implement data transfer from the trusted authority service provider to applications external to the implantable medical device and to the trusted authority service provider.

15. The trusted authority service provider of claim 11, wherein the performance manager is programmed to selectively implement adjustments to operation of the implantable medical device in treating sleep disordered breathing via the first secure communications.

16. The trusted authority service provider of claim 15, wherein the adjustment is at least partially based on sensed physiologic-related information.

17. The trusted authority service provider of claim 16, wherein the adjustment is based on data solely collected by the implantable medical device.

18. The trusted authority service provider of claim 16, wherein the adjustment is further based on performance information collected by the implantable medical device and a set of rules configurable by the clinician.

19. The trusted authority service provider of claim 1, wherein the controller is configured to execute machine readable instructions, stored in non-transitory memory, to implement via the communication element the first secure communications.

* * * * *